United States Patent [19]

Jaunin et al.

[11] Patent Number: 4,742,069
[45] Date of Patent: May 3, 1988

[54] SULFONAMIDE CONTAINING DIHYDROPYRIDINE DERIVATIVES, INTERMEDIATES AND MEDICINAL USE

[75] Inventors: Roland Jaunin, Basel; Henri Ramuz, Birsfelden, both of Switzerland

[73] Assignee: Hoffmann-La Roche Inc., Nutley, N.J.

[21] Appl. No.: 745,743

[22] Filed: Jun. 17, 1985

[30] Foreign Application Priority Data

Jun. 27, 1984 [CH] Switzerland ............ 3097/84

[51] Int. Cl.$^4$ ............ A61K 31/455; A61K 31/54; C07D 211/90; C07D 415/00
[52] U.S. Cl. ............ 514/356; 544/3; 546/322; 546/280; 564/80; 564/86; 564/95; 564/96; 564/97; 260/397.6; 260/397.7 R; 514/156; 514/166; 514/342
[58] Field of Search ............ 546/322, 280; 514/356, 514/222, 342; 544/3; 564/86, 97, 95, 80, 96

[56] References Cited

U.S. PATENT DOCUMENTS

| | | | |
|---|---|---|---|
| 4,162,321 | 7/1979 | Wehinger et al. | 546/322 |
| 4,188,395 | 2/1980 | Bossert et al. | 546/321 |
| 4,264,611 | 4/1981 | Berntsson et al. | 543/321 |
| 4,448,988 | 5/1984 | Günther | 564/95 |
| 4,532,248 | 7/1985 | Franckowiak et al. | 514/296 |

FOREIGN PATENT DOCUMENTS 2747513  5/1979  Fed. Rep. of Germany .

OTHER PUBLICATIONS

Burger, *Medicinal Chemistry*, second edition (1960) pp. 566, 568, 600, 601.

Primary Examiner—Richard A. Schwartz
Assistant Examiner—Dale A. Bjorkman
Attorney, Agent, or Firm—Jon S. Saxe; Bernard S. Leon; Matthew Boxer

[57] ABSTRACT

Dihydropyridine derivatives of the formula

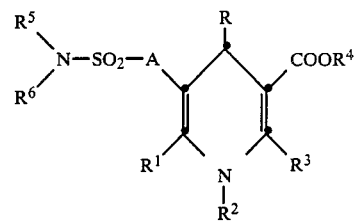

wherein the symbols A, R and $R^1$, $R^2$, $R^3$, $R^4$, $R^5$, $R^6$ and $R^7$ are as described herein.

Compounds of formula I have a pronounced calcium-antagonistic activity and can accordingly be used as medicaments, especially for the control or prevention of angina pectoris, ischemia, high blood pressure and/or migraine.

30 Claims, No Drawings

SULFONAMIDE CONTAINING DIHYDROPYRIDINE DERIVATIVES, INTERMEDIATES AND MEDICINAL USE

BRIEF SUMMARY OF THE INVENTION

The invention relates to dihydropyridine derivatives. In particular, it relates to dihydropyridine derivatives of the formula

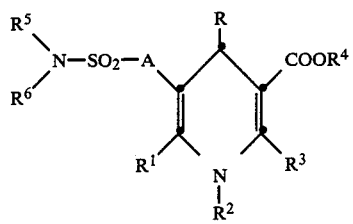

wherein A is the group —CH($R^7$)—CO— or

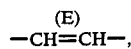

R is aryl or a heterocyclic residue with up to three hetero atoms selected from oxygen, nitrogen and sulfur, $R^1$ is hydrogen or methyl, $R^2$ is hydrogen or $C_1$–$C_4$-alkyl, $R^3$ is $C_1$–$C_4$-alkyl or $C_1$–$C_4$-alkanoyloxymethyl, $R^4$ is $C_1$–$C_6$-alkyl, $C_3$–$C_6$-alkenyl, $C_3$–$C_6$-alkynyl, $C_3$–$C_6$-cycloalkyl, $C_3$–$C_6$-cycloalkyl-$C_1$–$C_6$-alkyl, cyano-$C_2$–$C_6$-alkyl, halo-$C_2$–$C_6$-alkyl, hydroxy-$C_2$–$C_6$-alkyl, $\omega,\omega,\omega$-trifluoro-$C_1$–$C_6$-alkyl, $C_1$–$C_6$-alkoxy-$C_1$–$C_6$-alkyl, $C_1$–$C_6$-alkoxy-$C_1$–$C_6$-alkoxy-$C_1$–$C_6$-alkyl, $C_1$–$C_4$-alkanoyloxy-$C_1$–$C_6$-alkyl, $C_3$–$C_6$-alkenyloxy-$C_1$–$C_6$-alkyl, $C_1$–$C_6$-alkylthio-$C_1$–$C_6$-alkyl, benzyloxy-$C_1$–$C_6$-alkyl, phenyl optionally substituted by halogen, cyano, di-$C_1$–$C_6$-alkylamino, $C_1$–$C_6$-alkoxy, $C_1$–$C_6$-alkyl, trifluoromethyl or nitro or phenyl-$C_1$–$C_6$-alkyl optionally substituted by halogen, cyano, di-$C_1$–$C_6$-alkylamino, $C_1$–$C_6$-alkoxy, $C_1$–$C_6$-alkyl, trifluoromethyl or nitro, $R^5$ is $C_1$–$C_6$-alkyl or $C_3$–$C_6$-cycloalkyl, $R^6$ is hydrogen, $C_1$–$C_6$-alkyl, $C_3$–$C_6$-alkenyl, $C_3$–$C_6$-alkynyl, $C_3$–$C_6$-cycloalkyl, $C_3$–$C_6$-cycloalkyl-$C_1$–$C_6$-alkyl or phenyl-$C_1$–$C_6$-alkyl optionally substituted by $C_1$–$C_6$-alkyl, $C_1$–$C_6$-alkoxy or halogen and $R^7$ is hydrogen, $C_1$–$C_6$-alkyl or phenyl-$C_1$–$C_6$-alkyl optionally substituted by $C_1$–$C_6$-alkyl, $C_1$–$C_6$-alkoxy or halogen or $R^6$ and $R^7$ together are a —$(CH_2)_n$— group in which n is the number 2 or 3,
in the form of isomers, isomer mixtures, racemates and optical antipodes.

These compounds are useful in the control or prevention of illnesses or in the improvement of health, especially in the control or prevention of angina pectoris, ischemia, high blood pressure and migraine.

DETAILED DESCRIPTION OF THE INVENTION

The term "alkyl" used in the present description—alone or in combination—denotes straight-chain and branched, saturated hydrocarbon residues with the number of carbon atoms given in the respective case, such as methyl, ethyl, n-propyl, isopropyl, n-butyl, isobutyl, sec. butyl, tert.-butyl and the like. The term "alkoxy" denotes alkyl ether groups in which the term "alkyl" is as described above. The term "$C_3$–$C_6$-alkenyl" denotes straight-chain and branched hydrocarbon groups with 3–6 carbon atoms in which at least one carbon-carbon bond is unsaturated, such as allyl, butenyl and the like. The term "$C_3$–$C_6$-alkenyloxy" denotes alkenyl ether groups in which the term "$C_3$–$C_6$-alkenyl" is as described above. The term "$C_3$–$C_6$-alkynyl" denotes straight-chain and branched hydrocarbon groups with 3–6 carbon atoms in which at least one carbon-carbon triple bond is present, such as propargyl and the like. The term "$C_3$–$C_6$-cycloalkyl" denotes cyclic, saturated hydrocarbon residues with 3–6 carbon atoms, such as cyclopropyl, cyclohexyl and the like. The term "$C_1$–$C_4$-alkanoyloxy" denotes the acyloxy residue of an alkanecarboxylic acid with 1–4 carbon atoms, such as formyloxy, acetoxy, propionyloxy, butyryloxy and the like. The term "halogen" denotes fluorine, chlorine, bromine or iodine. The term "aryl" denotes a mono- or bicyclic aromatic hydrocarbon residue with up to 10 carbon atoms in the aromatic ring structure which is optionally mono-, di- or tri-substituted by phenyl, $C_1$–$C_6$-alkyl, $C_3$–$C_6$-alkenyl, $C_3$–$C_6$-alkynyl, $C_1$–$C_6$-alkoxy, halogen, trifluoromethyl, trifluoromethoxy, difluoromethoxy, trifluoromethylthio, difluoromethylthio, nitro, cyano, azido, $C_1$–$C_6$-alkoxycarbonyl, aminocarbonyl, aminosulfonyl, $C_1$–$C_6$-alkylthio, $C_1$–$C_6$-alkylsulfonyl or $C_1$–$C_6$-alkanoyl or which is optionally disubstituted by $C_3$–$C_5$-alkylene or dioxy-$C_1$–$C_2$-alkylene, such as chlorophenyl, tolyl, $\alpha,\alpha,\alpha$-trifluorotolyl, dichlorophenyl, chloronitrophenyl, naphthyl and the like. The term "heterocyclic residue" denotes 5- and 6-membered mono- and bicyclic heterocycles which are optionally mono-, di- or tri-substituted by phenyl, $C_1$–$C_6$-alkyl, $C_3$–$C_6$-alkenyl, $C_3$–$C_6$-alkynyl, $C_1$–$C_6$-alkoxy, halogen, trifluoromethyl, trifluoromethoxy, difluoromethoxy, trifluoromethylthio, difluoromethylthio, nitro, cyano, azido, $C_1$–$C_6$-alkoxycarbonyl, aminocarbonyl, aminosulfonyl, $C_1$–$C_6$-alkylthio, $C_1$–$C_6$-alkylsulfonyl or $C_1$–$C_6$-alkanoyl or which are optionally disubstituted by $C_3$–$C_5$-alkylene or dioxy-$C_1$–$C_2$-alkylene, such as thienyl, furyl, pyrryl, pyrazolyl, imidazolyl, oxazolyl, isoxazolyl, thiazolyl, isothiazolyl, pyridyl, N-oxidopyridyl, pyridazinyl, pyrimidyl, pyrazinyl, quinolyl, isoquinolyl, indolyl, benzimidazolyl, quinazolyl, quinoxalyl, (2,1,3-benzoxadiazol)-4-yl, (2,1,3-benzothiadiazol)-4-yl, benzofuranyl, benzothienyl, benzoxazolyl, benzisoxazolyl, benzothiazolyl, benzisothiazolyl, indazolyl and the like. The term "$C_1$–$C_6$-alkanoyl" denotes the acyl residue of an alkanecarboxylic acid with 1–6 carbon atoms, such as formyl, acetyl, propionyl, butyryl and the like. The term "leaving group" denotes known groups such as halogen, preferably iodine or bromine, arylsulfonyloxy, such as, for instance, tosyloxy or bromobenzenesulfonyloxy, or alkylsulfonyloxy, such as, for instance, mesyloxy. The symbol E is in

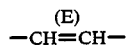

denotes a configuration wherein the hydrogens are on opposite sides of the double bond.

The invention relates to dihydropyridine derivatives. In particular, it relates to dihydropyridine derivatives of the formula

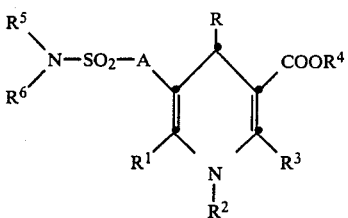

wherein A is the group —CH($R^7$)—CO— or $$\text{—CH=CH—,} \quad (E)$$

R is aryl or a heterocyclic residue with up to three hetero atoms selected from oxygen, nitrogen and sulfur, $R^1$ is hydrogen or methyl, $R^2$ is hydrogen or $C_1$–$C_4$-alkyl, $R^3$ is $C_1$–$C_4$-alkyl or $C_1$–$C_4$-alkanoyloxymethyl, $R^4$ is $C_1$–$C_6$-alkyl, $C_3$–$C_6$-alkenyl, $C_3$–$C_6$-alkynyl, $C_3$–$C_6$-cycloalkyl, $C_3$–$C_6$-cycloalkyl-$C_1$–$C_6$-alkyl, cyano-$C_2$–$C_6$-alkyl, halo-$C_2$–$C_6$-alkyl, hydroxy-$C_2$–$C_6$-alkyl, $\omega,\omega,\omega$-trifluoro-$C_1$–$C_6$-alkyl, $C_1$–$C_6$-alkoxy-$C_1$–$C_6$-alkyl, $C_1$–$C_6$-alkoxy-$C_1$–$C_6$-alkoxy-$C_1$–$C_6$-alkyl, $C_1$–$C_4$-alkanoyloxy-$C_1$–$C_6$-alkyl, $C_3$–$C_6$-alkenyloxy-$C_1$–$C_6$-alkyl, $C_1$–$C_6$-alkylthio-$C_1$–$C_6$-alkyl, benzyloxy-$C_1$–$C_6$-alkyl, phenyl optionally substituted by halogen, cyano, di-$C_1$–$C_6$-alkylamino, $C_1$–$C_6$-alkoxy, $C_1$–$C_6$-alkyl, trifluoromethyl or nitro or phenyl-$C_1$–$C_6$-alkyl optionally substituted by halogen, cyano, di-$C_1$–$C_6$-alkylamino, $C_1$–$C_6$-alkoxy, $C_1$–$C_6$-alkyl, trifluoromethyl or nitro, $R^5$ is $C_1$–$C_6$-alkyl or $C_3$–$C_6$-cycloalkyl, $R^6$ is hydrogen, $C_1$–$C_6$-alkyl, $C_3$–$C_6$-alkenyl, $C_3$–$C_6$-alkynyl, $C_3$–$C_6$-cycloalkyl, $C_3$–$C_6$-cycloalkyl-$C_1$–$C_6$-alkyl or phenyl-$C_1$–$C_6$-alkyl optionally substituted by $C_1$–$C_6$-alkyl, $C_1$–$C_6$-alkoxy or halogen and $R^7$ is hydrogen, $C_1$–$C_6$-alkyl or phenyl-$C_1$–$C_6$-alkyl optionally substituted by $C_1$–$C_6$-alkyl, $C_1$–$C_6$-alkoxy or halogen or $R^6$ and $R^7$ together are a —($CH_2$)$_n$— group in which n is the number 2 or 3, in the form of isomers, isomer mixtures, racemates and optical antipodes.

These compounds are novel and are distinguished by valuable pharmacodynamic properties.

Objects of the invention are compounds of formula I per se and for use as therapeutically active substances, the preparation of these compounds, intermediates for the preparation of these compounds, medicaments containing these compounds and the preparation of such medicaments, as well as the use of compounds of formula I in the control or prevention of illnesses or in the improvement of health, especially in the control or prevention of angina pectoris, ischemia, high blood pressure and migraine.

A particular class of compounds of formula I comprises those in which $R^4$ is $C_1$–$C_6$-alkyl, cyano-$C_2$–$C_6$-alkyl, halo-$C_2$–$C_6$-alkyl, hydroxy-$C_2$–$C_6$-alkyl, $\omega,\omega,\omega$-trifluoro-$C_1$–$C_6$-alkyl, $C_1$–$C_6$-alkoxy-$C_1$–$C_6$-alkyl, $C_1$–$C_4$-alkanoyloxy-$C_1$–$C_6$-alkyl, benzyloxy-$C_1$–$C_6$-alkyl or phenyl-$C_1$–$C_6$-alkyl optionally substituted by halogen, $R^5$ is $C_1$–$C_6$-alkyl, $R^6$ is hydrogen, $C_1$–$C_6$-alkyl, $C_3$–$C_6$-alkenyl or phenyl-$C_1$–$C_6$-alkyl, $R^7$ is hydrogen or $C_1$–$C_6$-alkyl or $R^6$ and $R^7$ together are a —($CH_2$)$_n$— group in which n is the number 2 or 3 and R is napthyl, phenyl optionally monosubstituted by $C_1$–$C_6$-alkyl, halogen, trifluoromethyl or nitro or optionally disubstituted by halogen or halogen and nitro, imidazolyl or pyridyl.

A preferred class of compounds of formula I comprises those in which A is the group —CH($R^7$)—CO—. Further, there are preferred those compounds of formula I wherein R is aryl, preferably phenyl substituted by $C_1$–$C_6$-alkyl, halogen, trifluoromethyl or nitro; especially wherein R is 3-nitrophenyl, 2-chloro-5-nitrophenyl or 2,5-dichlorophenyl. $R^1$ preferably is methyl. $R^2$ preferably is hydrogen. $R^3$ preferably is $C_1$–$C_4$-alkyl, particularly methyl. Further preferred compounds of formula I are those in which $R^4$ is $C_1$–$C_6$-alkyl, cyano-$C_2$–$C_6$-alkyl, halo-$C_2$–$C_6$-alkyl, hydroxy-$C_2$–$C_6$-alkyl, $\omega,\omega,\omega$-trifluoro-$C_1$–$C_6$-alkyl, $C_1$–$C_6$-alkoxy-$C_1$–$C_6$-alkyl, $C_1$–$C_4$-alkanoyloxy-$C_1$–$C_6$-alkyl, benzyloxy-$C_1$–$C_6$-alkyl or phenyl-$C_1$–$C_6$-alkyl optionally substituted by halogen, preferably $C_1$–$C_6$-alkyl, $\omega,\omega,\omega$-trifluoro-$C_1$–$C_6$-alkyl, $C_1$–$C_6$-alkoxy-$C_1$–$C_6$-alkyl or phenyl-$C_1$–$C_6$-alkyl, particularly isopropyl, 2,2,2-trifluoroethyl, 2-propoxyethyl or 1-phenylethyl. $R^5$ preferably is $C_1$–$C_6$-alkyl, particularly methyl, ethyl or isopropyl, $R^6$ and $R^7$ preferably are hydrogen.

From the above it follows that there are particularly preferred those compounds of formula I in which A is the group —CH($R^7$)—CO—, R is 3-nitrophenyl, 2-chloro-5-nitrophenyl or 2,5-dichlorophenyl, $R^1$ and $R^3$ each are methyl, $R^2$, $R^6$ and $R^7$ each are hydrogen, $R^4$ is isopropyl, 2,2,2-trifluoroethyl, 2-propoxyethyl or 1-phenylethyl and $R^5$ is methyl, ethyl or isopropyl.

The most preferred compounds of formula I are:

5-[(Ethylsulfamoyl)acetyl]-1,4-dihydro-2,6-dimethyl-4-(3-nitrophenyl)nicotinic acid isopropyl ester, 1,4-dihydro-2,6-dimethyl-5-[(methylsulfamoyl)acetyl]-4-(3-nitrophenyl)nicotinic acid isopropyl ester, 1,4-dihydro-2,6-dimethyl-5-[(methylsulfamoyl)-acetyl]-4-(3-nitrophenyl)nicotinic acid 2,2,2-trifluoroethyl ester, 4-(2-chloro-5-nitrophenyl)-1,4-dihydro-5-[(isopropylsulfamoyl)acetyl]-2,6-dimethylnicotinic acid isopropyl ester, 4-(2,5-dichlorophenyl)-1,4-dihydro-5-[(isopropylsulfamoyl)acetyl]-2,6-dimethylnicotinic acid isopropyl ester, 1,4-dihydro-5-[(isopropylsulfamoyl)acetyl]-2,6-dimethyl-4-(3-nitrophenyl)nicotinic acid 2-propoxyethyl ester and (S)-1,4-dihydro-5-[(isopropylsulfamoyl)acetyl]-2,6-dimethyl-4-(3-nitrophenyl)nicotinic acid (S)-1-phenylethyl ester.

The compounds of formula I above can be made as follows:

(a) for compounds of formula I in which A is the group —CH($R^7$)—CO—, i.e. of compounds of the formula

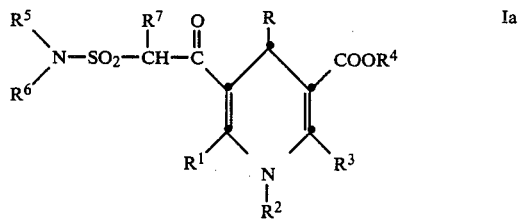

wherein R, $R^1$, $R^2$, $R^3$, $R^4$, $R^5$, $R^6$ and $R^7$ are as described above, reacting an enamine of the formula

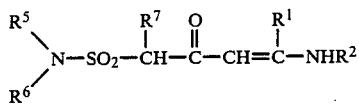

wherein $R^1$, $R^2$, $R^5$, $R^6$ and $R^7$ are as described above, with an ylidene compound of the formula

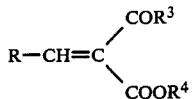

wherein R, $R^3$ and $R^4$ are as described above, or (b) for making the compounds of formula I in which A is the group

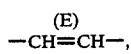

i.e. of compounds of the formula

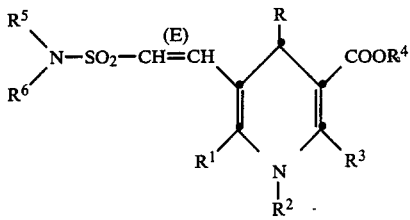

wherein R, $R^1$, $R^2$, $R^3$, $R^4$, $R^5$, $R^6$ and $R^7$ are as described above,
reacting a compound of formula Ia above in which $R^7$ is hydrogen with sodium borohydride, or (c) if desired, separating an isomer mixture obtained into the isomers.

The reaction of an enamine of formula II with an ylidene compound of formula III in accordance with process variant (a) is carried out according to methods known per se in the presence of an inert solvent or solvent mixture at a temperature between about 20° and 150° C., preferably at the reflux temperature of the solvent or solvent mixture. Suitable solvents for this purpose are, for example, alcohols such as methanol, ethanol or isopropanol, ethers such as diethyl ether, dioxan, tetrahydrofuran, glycol monomethyl ether or glycol dimethyl ether, glacial acetic acid, dimethylformamide, dimethyl sulfoxide, acetonitrile or pyridine. Although the pressure is not critical and the reaction can be carried out readily at elevated pressure, for reasons of convenience the reaction is preferably carried out at normal pressure. The two starting materials are preferably used in equimolar amounts.

The enamines of formula II are novel and are likewise an object of the invention. The enamines of formula II in which $R^6$ is hydrogen, i.e. the compounds of the formula

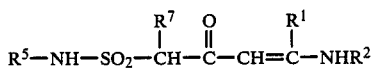

wherein $R^1$, $R^2$, $R^5$ and $R^7$ are as described above, can be prepared from 1,2-thiazin-5(6H)-one 1,1-dioxides of the formula

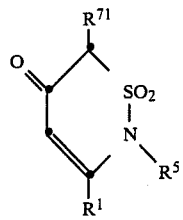

wherein $R^1$ and $R^5$ are as described above and $R^{71}$ is hydrogen, $C_1$–$C_6$-alkyl or phenyl-$C_1$–$C_6$-alkyl optionally substituted by $C_1$–$C_6$-alkyl, $C_1$–$C_6$-alkoxy or halogen,
by reaction with an amine of the formula $$R^2-NH_2 \qquad V$$

wherein $R^2$ is as described above.

The reaction is carried out according to methods known per se in the presence of an inert solvent such as an alcohol, for example methanol, ethanol or propanol, preferably methanol, at a temperature between about 0° and 40° C., preferably at room temperature. The 1,2-thiazin-5(6H)-one 1,1-dioxides of formula IV in which $R^{71}$ is hydrogen are known or can be prepared in an analogous manner to that described in the literature. Those in which $R^{71}$ is different from hydrogen can be obtained by alkylating those in which $R^{71}$ is hydrogen, i.e. 1,2-thiazin-5(6H)-one 1,1-dioxides of the formula

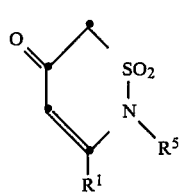

wherein $R^1$ and $R^5$ are as described above, with a compound of the formula $$R^{72}-X \qquad VI$$

wherein $R^{72}$ is $C_1$–$C_6$-alkyl or phenyl-$C_1$–$C_6$-alkyl optionally substituted by $C_1$–$C_6$-alkyl, $C_1$–$C_6$-alkoxy or halogen and X is a leaving group.

The alkylation with a compound of formula VI is carried out according to methods known per se, for example in the presence of a base such as sodium or potassium carbonate or potassium tert.-butylate in a solvent such as tert. butanol, benzene, toluene, diethyl ether, dioxan, tetrahydrofuran, dimethylformamide, dimethyl sulfoxide and the like at a temperature between about 0° and 50° C., preferably at room temperature. Where in the compound of formula VI $R^{71}$ is $C_1$–$C_6$-alkyl and X is halogen, the compound of formula VI thus being an alkyl halide, the alkylation can also be carried out in a two-phase system in the presence of a base and a phase-transfer catalyst, for example with an alkyl iodide in methylene chloride/aqueous sodium hydroxide solution in the presence of tetrabutylammonium hydrogen sulfate at a temperature between about 10° and 20° C.

The enamines of formula II in which $R^6$ is $C_1$–$C_6$-alkyl, $C_3$–$C_6$-alkenyl, $C_3$–$C_6$-alkynyl, $C_3$–$C_6$-cycloalkyl, $C_3$–$C_6$-cycloalkyl-$C_1$–$C_6$-alkyl or phenyl-$C_1$–$C_6$-alkyl optionally substituted by $C_1$–$C_6$-alkyl, $C_1$–$C_6$-alkoxy or halogen can be prepared by reacting an enamine of formula IIa above with a compound of the formula $$R^{61}-X \qquad \text{VII}$$

wherein $R^{61}$ is $C_1$–$C_6$-alkyl, $C_3$–$C_6$-alkenyl, $C_3$–$C_6$-alkynyl, $C_3$–$C_6$-cycloalkyl, $C_3$–$C_6$-cycloalkyl-$C_1$–$C_6$-alkyl or phenyl-$C_1$–$C_6$-alkyl optionally substituted by $C_1$–$C_6$-alkyl, $C_1$–$C_6$-alkoxy or halogen and X is as described above, according to methods known per se, preferably by reaction with a compound of formula VII in which X is halogen in the presence of base such as potassium carbonate in an inert solvent such as dimethylformamide at room temperature.

The enamines of formula II in which $R^6$ and $R^7$ together are a —$(CH_2)_n$— group can be prepared from the enamines of formula IIa and a compound of the formula $$X-(CH_2)_n-X \qquad \text{VIII}$$

wherein X and n are as described above in an analogous manner to that described above for the reaction of an enamine of formula IIa with a compound of formula VII.

The ylidene compounds of formula III are already known or can be obtained according to known methods, for example by reacting a β-ketocarboxylic acid ester of the formula $$R^3-\overset{\overset{O}{\|}}{C}-CH_2-COOR^4 \qquad \text{IX}$$

wherein $R^3$ and $R^4$ are as described above, with an aldehyde of the formula $$RCHO \qquad X$$

wherein R is as described above.

The ylidene compound of formula III obtained need not be isolated prior to its reaction with an enamine of formula II; on the contrary, for the making of compounds of formula Ia the compounds of formulae II, IX and X can be reacted with one another, preferably in equimolar amounts, under the reaction conditions described for the reaction of an enamine of formula II with an ylidene compound of formula III, whereby the desired compound of formula Ia is obtained directly.

The starting materials of formulae IX and X above are known or can be obtained in an analogous manner to the preparation of the known compounds.

The reaction of a compound of formula Ia in which $R^7$ is hydrogen with sodium borohydride with simultaneous reduction and dehydration in accordance with process variant (b) is carried out according to methods known per se, conveniently in an organic solvent such as an alcohol, for example ethanol, propanol, isopropanol and the like, or a mixture of an alcohol with dimethylformamide or 1,2-dimethoxy ether at a temperature between about 0° and 50° C., preferably at room temperature.

The compounds of formula I contain at least one asymmetric centre (4-position) and can therefore exist as optical antipodes or as racemates. Compounds of formula I which contain more than one asymmetric centre can exist in various diastereoisomeric forms. The invention relates to all possible stereoisomers of compounds of formula I and all possible diastereoisomeric mixtures and racemates, as well as the separation of these diastereoisomeric mixtures which can be carried out according to methods known per se.

The compounds of formula I have a pronounced calcium-antagonistic activity and can accordingly be used as medicaments, especially for the control or prevention of angina pectoris, ischemia, high blood pressure and migraine.

The calcium-antagonistic activity as well as the blood pressure-lowering properties of the compounds in accordance with the invention can be demonstrated in the tests described hereinafter:

A. $^3$H-Nifedipine binding determinations:

The determination is carried out on homogenates or on partially-cleaned membranes of rabbit or guinea pig heart. The reaction mixture (0.3 ml) consists of 0.2–0.8 mg of membrane protein, 1 nM of $^3$H-nifedipine (or 0.25 nM of $^3$H-nitrendipine) and various concentrations of the test substances. The incubation lasts 30 minutes at 25° C. or 37° C. and is stopped by dilution with the incubation buffer; a filtration is subsequently carried out. The filter-bound radioactivity is measured with a scintillation counter. Specific binding (i.e. receptor-bound) is defined as the difference between total and unspecific-bound radioactivity. The unspecific binding is determined in the presence of an excess of non-radioactive nifedipine (1 μM).

The activity (potency) of a compound in this test is defined by the $IC_{50}$ and % maximum inhibition values (% max. inhibition). The $IC_{50}$ is the substance concentration (in mol/l) which produces a half-maximum inhibition of the specific $^3$H-nifedipine (or $^3$H-nitrendipine) binding. In the table compound A has an $IC_{50}$ in mol/l, of $3.0 \cdot 10^{-8}$ which means $3.0 \times 10^{-8}$. The maximum inhibition of the specific binding is given by the % maximum inhibition value; this value is established as 100% for the reference compound nifedipine. Both parameters are extrapolated from a concentration-binding curve.

B. Coronary artery strips of dogs:

In this experiment spiral strips (2–2.5 mm wide and 10 mm long) of coronary arteries of dogs are cut and hung up in an organ chamber under an initial tension of 1.5 g. These strips are pre-incubated for a duration of about 1 to 2 hours in Krebs-Henseleit buffer solution which is gassed with Oxycarbon (a mixture of 95% oxygen and 5% carbon dioxide) at 37° C. The relaxing activity of one of these substances is subsequently tested on a KCl (84.7 mM) contracture by the addition of increasing concentrations of the test substance to the organ chamber. The calcium channel-blocking activity of the test substances can therefore be established, as the KCl contracture occurs exclusively by means of calcium flow through the tension-dependent calcium channel.

The activity of a test substance in this test is given by the $IC_{50}$ value. This value is defined as the substance concentration (in mol/l) which produces a half-maximum relaxation of a KCl contracture. This value is also extrapolated from the resulting concentration-activity curve.

C. Hemodynamic parameters in the narcotized dog:

The 4 most important measurement parameters (with respective measurement units) of the hemodynamic experiment are: (1) CBF: Coronary Blood Flow (in ml/min)—the velocity of blood flow through the coronary arteries; (2) HR: heart rate (in beats/min)—the heart frequency; (3) BP: blood pressure (in mm Hg); and (4) dp/dt: rate of increase in left ventricular pressure (in mm Hg/sec) as a measurement of the contractility force of the heart. The values are given as the % maximum variation from the initial value ($\Delta\%$) and the duration in minutes of this variation (t) per dosage administered.

There is thus obtained not only an overall picture of the activity of the substance, but also an estimation as to the potential selectivity for a specific part of the circulatory system in the entire organism. After the administration of an anesthetic, the dog is intubated and respired artificially. Blood pH, $pCO_2$, $pO_2$ and hemoglobin are measured hourly with a blood-gas analyzer. The blood pressure (systolic and diastolic) is measured with a probe in the aorta abdominalis. The heart frequency is recorded by means of a tachometer, which is disengaged from the pressure pulse. For the other measurements the heart must first be opened in order that a probe can be inserted in the left ventricle (heart chamber) for the pressure measurements (dp/dt). The coronary blood flow is measured with a flowing probe in the left coronary artery (descendens).

The results obtained in these tests are compiled in the following Table. This Table shows that representative compounds of the invention possess coronary dilating and blood pressure lowering properties. This allows the prediction that they are useful as agents in the control or prevention of angina pectoris, ischemia, high blood pressure and migraine.

gelatine capsules, lactose, maize starch or derivatives thereof, talc, stearic acid or its salts etc.

For soft gelatine capsules there are suitable as excipients e.g. vegetable oils, waxes, fats, semi-solid and liquid polyols etc.

For making solutions and syrups there are suitable as excipients e.g. water, polyols, saccharose, invert sugar, glucose etc.

For injection solutions there are suitable as excipients e.g. water, alcohols, polyols, glycerine, vegetable oils etc.

For suppositories there are suitable as excipients e.g. natural or hardened oils, waxes, fats, semi-liquid or liquid polyols etc.

Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

In accordance with the invention compounds of formula I can be used in the control or prevention of angina pectoris, ischemia, high blood pressure and migraine. The dosage can vary within wide limits and will, of course, be adjusted to the individual requirements in each particular case. In general, in the case of oral administration a daily dosage of about 10 to 100 mg of a compound of formula I should be appropriate, whereby, however, the upper limit just given can also be exceeded when this is shown to be indicated.

The following Examples are intended to illustrate the invention, but they are not intended to be limiting in any manner. All temperatures are given in degrees Celsius.

TABLE

| Compound | A | | B | C | | | | |
|---|---|---|---|---|---|---|---|---|
| | $IC_{50}$ [M] | % max. inhib. | $IC_{50}$ [M] | CBF ml/min. t | HR beats/min. t | Bp mm Hg t | dp/dt mm Hg/sec. t | Dosage mg/kg. p.o. |
| A | $3.0 \cdot 10^{-8}$ | 100 | $6.8 \cdot 10^{-9}$ | 98(90°) | −11(60°) | −13(>60°) | 37(90°) | 0.03 |
| B | $8.4 \cdot 10^{-8}$ | 94 | $1.6 \cdot 10^{-8}$ | 120(>90°) | 0 | −8(>90°) | 10(>90°) | 0.03 |
| C | $4.2 \cdot 10^{-8}$ | 100 | $9.5 \cdot 10^{-9}$ | 88(180°) | +2(120°) | −16(>180°) | 33(180°) | 0.1 |
| D | $1.5 \cdot 10^{-7}$ | 100 | $8.2 \cdot 10^{-10}$ | 68(>120°) | −5(60°) | −9(>60°) | 75(90°) | 0.03 |
| E | $2.9 \cdot 10^{-8}$ | 100 | $6.6 \cdot 10^{-9}$ | 104(70°) | −14(120°) | −16(>120°) | 65(90°) | 0.03 |
| F | $2.7 \cdot 10^{-9}$ | 99 | $6.0 \cdot 10^{-10}$ | 56(120°) | −5(16°) | −11(>60°) | 34(60°) | 0.03 |
| G | $4.0 \cdot 10^{-9}$ | 100 | $7.4 \cdot 10^{-9}$ | 57(>120°) | −13(>120°) | −36(>120°) | 29(>120°) | 0.03 |

A = 5-[(Ethylsulphamoyl)acetyl]-1,4-dihydro-2,6-dimethyl-4-(3-nitrophenyl)nicotinic acid isopropyl ester
B = 1,4-Dihydro-2,6-dimethyl-5-[(methylsulphamoyl)acetyl]-4-(3-nitrophenyl)nicotinic acid isopropyl ester
C = 1,4-Dihydro-2,6-dimethyl-5-[(methylsulphamoyl)acetyl]-4-(3-nitrophenyl)nicotinic acid 2,2,2-trifluoroethyl ester.
D = 4-(2-Chloro-5-nitrophenyl)-1,4-dihydro-5-[(isopropylsulphamoyl)acetyl]-2,6-dimethylnicotinic acid isopropyl ester
E = 4-(2,5-Dichlorophenyl)-1,4-dihydro-5-[(isopropylsulphamoyl)acetyl]-2,6-dimethylnicotinic acid isopropyl ester
F = 1,4-Dihydro-5-[(isopropylsulphamoyl)acetyl]-2,6-dimethyl-4-(3-nitrophenyl)nicotinic acid 2-propoxyethyl ester
G = (S)-1,4-Dihydro-5-[(isopropylsulphamoyl)acetyl]-2,6-dimethyl-4-(3-nitrophenyl)nicotinic acid (S)-1-phenyl ethyl ester The compounds of formula I can be used as medicaments, e.g. in the form of pharmaceutical preparations comprising a compound of formula I and a pharmaceutically acceptable carrier material. Pharmaceutically acceptable carrier materials are known to those skilled in the art and can include those listed below. The pharmaceutical preparations can be administered orally, e.g. in the form of tablets, coated tablets, dragees, hard and soft gelatine capsules, solutions, emulsions or suspensions. The administration can, however, also be carried out rectally, e.g. in the form of suppositories, or parenterally, e.g. in the form of injection solutions.

For the manufacture of tablets, coated tablets, dragees and hard gelatine capsules the compounds of formula I can be processed with pharmaceutically inert, inorganic or organic excipients. As such excipients there can be used e.g. for tablets, dragees and hard

EXAMPLE 1

A solution of 4.88 g of 3-nitrobenzylidineacetoacetic acid methyl ester in a mixture of 20 ml of isopropanol and 10 ml of dimethylformamide was treated under agron with 3.84 g of 4-amino-N-methyl-2-oxo-3-pentenesulfonamide and the mixture was thereupon heated to reflux for 8 hours. The solution was then concentrated to dryness under reduced pressure and the residual yellow oil was chromatographed on 500 g of silica gel with ethyl acetate as the elution agent. The uniform fractions were combined and evaporated. After triturating the residue with ether there were obtained 3.8 g of 1,4-dihydro-2,6-dimethyl-5-[(methylsulfamoyl)acetyl]-4-(3-nitrophenyl)nicotinic acid methyl ester, m.p. 173°–176°, as a yellow crystalline powder. Recrystallization from ethanol did not increase the melting point.

The 4-amino-N-methyl-2-oxo-3-pentenesulfonamide used as the starting material was prepared as follows:

A moderately rapid stream of dry ammonia was introduced at 20°–25° during 3 hours into a suspension of 10 g of 2,3-dimethyl-1,2-thiazin-5(6H)-one 1,1-dioxide in 100 ml of methanol, whereby a clear pale yellow solution resulted after about 10–15 minutes. Thereupon, the mixture was stirred further at room temperature overnight. The crystallized-out product was filtered off and washed with a small amount of methanol, whereby there were obtained 9.8 g of 4-amino-N-methyl-2-oxo-3-pentenesulfonamide in the form of colorless crystals, m.p. 158°–162°. From the filtrate there were obtained by concentration to about 50 ml an additional 2.2 g of product, mp. 158°–162°, total yield: 12 g.

EXAMPLE 2

The following compounds were made in a manner analogous to that described in Example 1:

1,4-Dihydro-2,6-dimethyl-5-[(methylsulfamoyl)acetyl]-4-(3-nitrophenyl)nicotinic acid 2-chloroethyl ester, m.p. 101°–105°, from 3-nitrobenzylideneacetoacetic acid 2-chloroethyl ester and 4-amino-N-methyl-2-oxo-3-pentenesulfonamide;

1,4-dihydro-2,6-dimethyl-5-[(methylsulfamoyl)acetyl]-4-(3-nitrophenyl)nicotinic acid 2-propoxyethyl ester, m.p. 106°–110°, from 3-nitrobenzylideneacetoacetic acid 2-propoxyethyl ester and 4-amino-N-methyl-2-oxo-3-pentenesulfonamide;

1,4-dihydro-2,6-dimethyl-5-[(methylsulfamoyl)acetyl]-4-(3-nitrophenyl)nicotinic acid 3-chloropropyl ester, m.p. 96°–101° (crystallizing with 0.5 mol of ethanol), from 3-nitrobenzylideneacetoacetic acid 3-chloropropyl ester and 4-amino-N-methyl-2-oxo-3-pentenesulfonamide;

1,4-dihydro-2,6-dimethyl-5-[(methylsulfamoyl)acetyl]-4-(3-nitrophenyl)nicotinic acid isopropyl ester, m.p. 177°–180°, from 3-nitrobenzylideneacetoacetic acid isopropyl ester and 4-amino-N-methyl-2-oxo-3-pentenesulfonamide;

1,4-dihydro-2,6-dimethyl-5-[(methylsulfamoyl)acetyl]-4-(3-nitrophenyl)nicotinic acid 2,2,2-trifluoroethyl ester, m.p. 135°–140° (crystallizing with 0.5 mol of ethanol), from 3-nitrobenzylideneacetoacetic acid 2,2,2-trifluoroethyl ester and 4-amino-N-methyl-2-oxo-3-pentenesulfonamide and 1,4-dihydro-2,6-dimethyl-5-[(methylsulfamoyl)acetyl]-4-(2-nitrophenyl)nicotinic acid isopropyl ester, m.p.156°–158° (crystallizing with 0.5 mol of ethanol), from 2-nitrobenzylideneacetoacetic acid isopropyl ester and 4-amino-N-methyl-2-oxo-3-pentenesulfonamide.

EXAMPLE 3

A solution of 5.54 g of 3-nitrobenzylideneacetoacetic acid isopropyl ester in 20 ml of isopropanol and 10 ml of dimethylformamide was treated under argon with 4.12 g of N-ethyl-4-amino-2-oxo-3-pentenesulfonamide and the mixture was heated to reflux for 8 hours. The mixture was thereupon concentrated to dryness under reduced pressure and the oily residue was chromatographed on 500 g of silica gel with methylene chloride/ethyl acetate (4:1) as the elution agent. The homogeneous fractions were combined and evaporated. The residual oil crystallized upon trituration with ether. Recrystallization from ethanol/ether yielded 5.0 g of 5-[(ethylsulfamoyl)acetyl]-1,4-dihydro-2,6-dimethyl-4-(3-nitrophenyl)nicotinic acid isopropyl ester in the form of yellow crystals, m.p. 140°–142°.

The N-ethyl-4-amino-2-oxo-3-pentenesulfonamide used as the starting material was prepared as follows:

A solution, cooled to −75°, of 24.5 g of 1-methyl-1,3-bis(trimethylsiloxy)-1,3-butadiene and 10.1 g of triethylamide in 100 ml of dry tetrahydrofuran was treated dropwise at −80° to −70° under argon with a solution of 14.4 g of N-ethyl-sulfamoyl chloride in 50 ml of dry tetrahydrofuran and the mixture was subsequently stirred at the same temperature for 2 hours. The temperature was then allowed to rise to room temperature, the mixture was stirred for 1 hour, acidified at 15°–20° with 110 ml of 2N hydrochloric acid and stirred for a further 15 minutes. The mixture was extracted with ether and the extracts, dried over sodium sulfate, were evaporated to dryness. The residual oil was dissolved in 250 ml of toluene, 0.4 g of methanesulfonic acid was added thereto and the mixture was heated to reflux for 15 hours with a water separator. The solution obtained was cooled, concentrated to dryness under reduced pressure and the residual oil was chromatographed on 280 g of silica gel with methylene chloride/ethyl acetate (9:1) as the elution agent. The uniform fractions were combined and evaporated. After triturating the residue with ether there were obtained 13.8 g of 2-ethyl-3-methyl-1,2-thiazin-5-(6H)-one 1,1-dioxide in the form of almost colorless crystals, m.p. 90°–92°. Recrystallization from ethanol did not increase the melting point.

A suspension of 13 g of 2-ethyl-3-methyl-1,2-thiazin-5(6H)-one 1,1-dioxide in 130 ml of methanol was reacted with ammonia in accordance with the procedure described in Example 1. The dark yellow solution obtained was concentrated to dryness under reduced pressure and the crystalline residue was recrystallized from ethanol. There were obtained 12.2 g of N-ethyl-4-amino-2-oxo-3-pentenesulfonamide in the form of colorless crystals, m.p. 112°–114°.

EXAMPLE 4

A solution of 5.54 g of 3-nitrobenzylideneacetoacetic acid isopropyl ester in a mixture of 50 ml of isopropanol and 24 ml of dimethylformamide was treated under argon with 4.40 g of 4-amino-N-isopropyl-2-oxo-3-pentenesulfonamide and the mixture was thereupon heated to reflux for 16 hours. After concentration under reduced pressure the oily residue was chromatographed on 300 g of silica gel with methylene chloride/ethyl acetate (4:1) as the elution agent. The homogeneous fractions yielded an oil which crystallized by trituration with ether. There were obtained 10.8 g of 1,4-dihydro-5-[(isopropylsulfamoyl)acetyl]-2,6-dimethyl-4-(3-nitrophenyl)nicotinic acid isopropyl ester in the form of yellow crystals, m.p. 119°–121°. Recrystallization from methylene chloride/ether did not increase the melting point.

The 4-amino-N-isopropyl-2-oxo-3-pentenesulfonamide used as the starting material was prepared as follows:

A suspension of 10 g of 2-isopropyl-3-methyl-1,2-thiazin-5(6H)-one 1,1-dioxide in 100 ml of methanol was reacted with ammonia in accordance with the procedure described in Example 1. The solution obtained was concentrated to dryness under reduced pressure and the solid residue was recrystallized from isopropanol. There were obtained 10.1 g of 4-amino-N-isopropyl-2-oxo-3-pentenesulfonamide in the form of colorless crystals, m.p. 119°–121°.

EXAMPLE 5

The following compounds were made in a manner analogous to that described in Example 4:

1,4-Dihydro-5-[(isopropylsulfamoyl)acetyl]-2,6-dimethyl-4-(3-nitrophenyl)nicotinic acid methyl ester, m.p. 208°–212°, from 3-nitrobenzylideneacetoacetic acid methyl ester and 4-amino-N-isopropyl-2-oxo-3-pentenesulfonamide;

1,4-dihydro-5-[(isopropylsulfamoyl)acetyl]-2,6-dimethyl-4-(3-trifluoromethylphenyl)nicotinic acid methyl ester, m.p. 184°–187°, from 3-trifluoromethylbenzylideneacetoacetic acid methyl ester and 4-amino-N-isopropyl-2-oxo-3-pentenesulfonamide;

1,4-dihydro-5-[(isopropylsulfamoyl)acetyl]-2,6-dimethyl-4-(3-nitrophenyl)nicotinic acid 2-chloroethyl ester, m.p. 121°–125°, from 3-nitrobenzylideneacetoacetic acid 2-chloroethyl ester and 4-amino-N-isopropyl-2-oxo-3-pentenesulfonamide;

1,4-dihydro-5-[(isopropylsulfamoyl)acetyl]-2,6-dimethyl-4-(3-nitrophenyl)nicotinic acid isobutyl ester, m.p. 75°–79°, from 3-nitrobenzylideneacetoacetic acid isobutyl ester and 4-amino-N-isopropyl-2-oxo-3-pentenesulfonamide;

4-(2,3-dichlorophenyl)-1,4-dihydro-5-[(isopropylsulfamoyl)acetyl]-2,6-dimethylnicotinic acid isopropyl ester, m.p. 152°–154°, from 2,3-dichlorobenzylideneacetoacetic acid isopropyl ester and 4-amino-N-isopropyl-2-oxo-3-pentenesulfonamide;

1,4-dihydro-5-[(isopropylsulfamoyl)acetyl]-2,6-dimethyl-4-(3-nitrophenyl)nicotinic acid ethyl ester, m.p. 124°–126°, from 3-nitrobenzylideneacetoacetic acid ether ester and 4-amino-N-isopropyl-2-oxo-3-pentenesulfonamide;

1,4-dihydro-5-[(isopropylsulfamoyl)acetyl]-2,6-dimethyl-4-(3-nitrophenyl)nicotinic acid propyl ester, m.p. 76°–80°, from 3-nitrobenzylideneacetoacetic acid propyl ester and 4-amino-N-isopropyl-2-oxo-3-pentenesulfonamide;

1,4-dihydro-5-[(isopropylsulfamoyl)acetyl]-2,6-dimethyl-4-(3-nitrophenyl)nicotinic acid 2-(benzyloxy)ethyl ester, m.p. 144°–147°, from 3-nitrobenzylideneacetoacetic acid 2-(benzyloxy)ethyl ester and 4-amino-N-isopropyl-2-oxo-3-pentenesulfonamide;

1,4-dihydro-5-[(isopropylsulfamoyl)acetyl]-2,6-dimethyl-4-(3-nitrophenyl)nicotinic acid 2,2,2-trifluoroethyl ester, m.p. 138°–141°, from 3-nitrobenzylideneacetoacetic acid 2,2,2-trifluoroethyl ester and 4-amino-N-isopropyl-2-oxo-3-pentenesulfonamide;

1,4-dihydro-5-[(isopropylsulfamoyl)acetyl]-4-(imidazol-2yl)-2,6-dimethylnicotinic acid isopropyl ester, m.p. 227°–229°, from 2-imidazolyl-methyleneacetoacetic acid isopropylester and 4-amino-N-isopropyl-2-oxo-3-pentenesulfonamide;

4-(2-chloro-5-nitrophenyl)-1,4-dihydro-5-[(isopropylsulfamoyl)acetyl]-2,6-dimethylnicotinic acid isopropyl ester, m.p. 195°–197°, from 2-chloro-5-nitrobenzylideneacetoacetic acid isopropyl ester and 4-amino-N-isopropyl-2-oxo-3-pentenesulfonamide;

1,4-dihydro-5-[(isopropylsulfamoyl)acetyl]-2,6-dimethyl-4-(2-nitrophenyl)nicotinic acid isopropyl ester, m.p. 175°–177° (crystallizing with 0.5 mol of ethanol), from 2-nitrobenzylideneacetoacetic acid isopropyl ester and 4-amino-N-isopropyl-2-oxo-3-pentenesulfonamide;

1,4-dihydro-5-[(isopropylsulfamoyl)acetyl]-2,6-dimethyl-4-(1-naphthyl)nicotinic acid isopropyl ester, m.p. 187°–189°, from 1-naphthyl-methyleneacetoacetic acid isopropyl ester and 4-amino-N-isopropyl-2-oxo-3-pentenesulfonamide;

4-(2,5-dichlorophenyl)-1,4-dihydro-5-[(isopropylsulfamoyl)acetyl]-2,6-dimethylnicotinic acid isopropyl ester, m.p. 158°–160°, from 2,5-dichlorobenzylideneacetoacetic acid isopropyl ester and 4-amino-N-isopropyl-2-oxo-3-pentenesulfonamide;

1,4-dihydro-5-[(isopropylsulfamoyl)acetyl]-2,6-dimethyl-4-(3-pyridyl)nicotinic acid isopropyl ester, m.p. 179°–181°, from 3-pyridyl-methyleneacetoacetic acid isopropyl ester and 4-amino-N-isopropyl-2-oxo-3-pentenesulfonamide;

1,4-dihydro-5-[(isopropylsulfamoyl)acetyl]-2,6-dimethyl-4-(2-tolyl)nicotinic acid isopropyl ester, m.p. 163°–166°, from 2-methylbenzylideneacetoacetic acid isopropyl ester and 4-amino-N-isopropyl-2-oxo-3-pentenesulfonamide;

1,4-dihydro-5-[(isopropylsulfamoyl)acetyl]-2,6-dimethyl-4-(3-nitrophenyl)nicotinic acid 2-propoxyethyl ester, m.p. 103°–106°, from 3-nitrobenzylideneacetoacetic acid 2-propoxyethyl ester and 4-amino-N-isopropyl-2-oxo-3-pentenesulfonamide;

1,4-dihydro-5-[(isopropylsulfamoyl)acetyl]-2,6-dimethyl-4-(3-nitrophenyl)nicotinic acid 2-methoxyethyl ester, m.p. 133°–136°, from 3-nitrobenzylideneacetoacetic acid 2-methoxyethyl ester and 4-amino-N-isopropyl-2-oxo-3-pentenesulfonamide and 4-(2-chloro-5-nitrophenyl)-1,4-dihydro-5-[(isopropylsulfamoyl)acetyl]-2,6-dimethylnicotinic acid 2-cyanoethyl ester, m.p. 196°–198°, from 2-chloro-5-nitrobenzylideneacetoacetic acid 2-cyanoethyl ester and 4-amino-N-isopropyl-2-oxo-3-pentenesulfonamide.

EXAMPLE 6

After boiling 2.5 g of 3-nitrobenzylideneacetoacetic acid methyl ester and 1.92 g of N-ethyl-4-amino-2-oxo-3-butenesulfonamide in a mixture of 10 ml of isopropanol and 5 ml of dimethylformamide for 6 hours there were obtained 2.2 g of 5-[(ethylsulfamoyl)acetyl]-1,4-dihydro-2-methyl-4-(3-nitrophenyl)nicotinic acid methyl ester of melting point 185°–187° (yellow crystalline powder from acetonitrile).

For the preparation of the N-ethyl-4-amino-2-oxo-3-butenesulfonamide used as the starting material, 5 g of 2-ethyl-1,2-thiazin-5(6H)-one 1,1-dioxide in 50 ml of methanol were reacted with ammonia in accordance with the procedure described in Example 1. There were obtained 4.8 g of colorless crystals, m.p. 96°–98° (from ether).

EXAMPLE 7

After boiling 2.5 g of 3-nitrobenzylidene-acetoacetic acid methyl ester and 2.06 g of 4-amino-N,N-dimethyl-2-oxo-3-pentenesulfonamide is a mixture of 10 ml of isopropanol and 5 ml of dimethylformamide for 6 hours there were obtained 2.3 g of 1,4-dihydro-2,6-dimethyl-5-[(dimethylsulfamoyl)acetyl]-4-(3-nitrophenyl)nicotinic acid methyl ester of melting point 154°–157° (yellow crystalline powder from ethanol).

The 4-amino-N,N-dimethyl-2-oxo-3-pentenesulfonamide used as the starting material was prepared as follows:

A solution of 3.8 g of 4-amino-N-methyl-2-oxo-3-pentenesulfonamide and 1.9 ml of methyl iodide in 50 ml of dimethylformamide was treated with 6 g of finely ground dry potassium carbonate and the mixture was thereupon stirred intensively at room temperature under argon for 6 hours. The organic salts were then filtered off, rinsed with methylene chloride and the filtrate was concentrated to dryness under reduced pressure. The residue was partitioned between water and methylene chloride, the organic phase was washed with a saturated aqueous solution of sodium chloride, dried over sodium sulfate and evaporated to dryness. The solid product was recrystallized from isopropanol, whereby there were obtained 2.5 g of 4-amino-N,N-dimethyl-2-oxo-3-pentenesulfonamide in the form of colorless crystals, m.p. 137°-140°.

EXAMPLE 8

After boiling 2.5 g of 3-nitrobenzylideneacetoacetic acid methyl ester and 2.82 g of 4-amino-N-benzyl-N-methyl-2-oxo-3-pentenesulfonamide in a mixture of 16 ml of isopropanol and 8 ml of dimethylformamide for 8 hours there were obtained 2.7 g of 5-[(benzylmethylsulfamoyl)acetyl]-1,4-dihydro-2,6-dimethyl-4-(3-nitrophenyl)nicotinic acid methyl ester of melting point 156°-159° (yellow crystalline powder from acetonitrile).

The 4-amino-N-benzyl-N-methyl-2-oxo-3-pentenesulfonamide used as the starting material was prepared as follows:

In accordance with the procedure described in Example 7, a solution of 3.8 g of 4-amino-N-methyl-2-oxo-3-pentenesulfonamide and 3.6 ml of benzyl bromide in 50 ml of dimethylformamide was treated with 6 g of potassium carbonate and the mixture was stirred intensively at room temperature for 9 hours. The product was firstly chromatographed on 300 g of silica gel with ethyl acetate as the elution agent and then recrystallized from isopropanol. There were obtained 3.4 g of 4-amino-N-benzyl-N-methyl-2-oxo-3-pentenesulfonamide in the form of colorless crystals, m.p. 115°-118°.

EXAMPLE 9

After boiling 2.77 g of 3-nitrobenzylideneacetoacetic acid isopropyl ester and 2.32 g of N-allyl-N-methyl-4-amino-2-oxo-3-pentenesulfonamide in a mixture of 25 ml of isopropanol and 12 ml of dimethylformamide for 8 hours there were obtained 1.9 g of 5-[(allylmethylsulfamoyl)acetyl]-1,4-dihydro-2,6-dimethyl-4-(3-nitrophenyl)nicotinic acid isopropyl ester of melting point 137°-140° (yellow crystalline powder from ethanol).

The N-allyl-N-methyl-4-amino-2-oxo-3-pentenesulfonamide used as the starting material was prepared as follows:

In accordance with the procedure described in Example 7, a solution of 3.8 g of 4-amino-N-methyl-2-oxo-3-pentenesulfonamide and 2.5 ml of allyl bromide in 50 ml of dimethylformamide was treated with 6 g of potassium carbonate and the mixture was stirred intensively at room temperature for 7 hours. The product was firstly chromatographed on 300 g of silica gel with methylene chloride/ethyl acetate (4:1) as the elution agent and then recrystallized from methylene chloride/ether. There were obtained 3.3 g of N-allyl-N-methyl-4-amino-2-oxo-3-pentenesulfonamide in the form of colorless crystals, m.p. 86°-89°.

EXAMPLE 10

After boiling 2.98 g of 3-nitrobenzylideneacetoacetic acid 2-chloroethyl ester and 2.18 g of 5-(3-aminocrotonyl)-2-methylthiazolidine 1,1-dioxide in a mixture of 15 ml of isopropanol and 5 ml of dimethylformamide for 8 hours there were obtained 2.85 g of 1,4-dihydro-2,6-dimethyl-5-[(2'-methyl-5'-thiazolidinyl)carbonyl]-4-(3-nitrophenyl)nicotinic acid 2-chloroethyl ester 1',1'-dioxide as a diastereoisomeric mixture of melting point 239°-242° (yellow crystalline powder from acetonitrile).

The 5-(3-aminocrotonyl)-2-methylthiazolidine 1,1-dioxide used as the starting material was prepared as follows:

In accordance with the procedure described in Example 7, a solution of 3.8 g of 4-amino-N-methyl-2-oxo-3-pentenesulfonamide and 4 ml of ethylene bromide in 50 ml of dimethylformamide were treated with 12 g of potassium carbonate and the mixture was stirred intensively at 80° in an oil bath for 6 hours. The product was firstly chromatographed on 300 g of silica gel with methylene chloride/ethyl acetate (1:1) as the elution agent and then recrystallized from ethanol. There were obtained 1.9 g of 5-(3-aminocrotonyl)-2-methylthiazolidine 1,1-dioxide in the form of colorless crystals, m.p. 113°-115°.

EXAMPLE 11

After boiling 3.2 g of 3-nitrobenzylideneacetoacetic acid 2-propoxyethyl ester and 2.05 g of 4-amino-N,1-dimethyl-2-oxo-3-pentenesulfonamide in a mixture of 10 ml of isopropanol and 5 ml of dimethylformamide for 8 hours there were obtained 1.7 g of 1,4-dihydro-2,6-dimethyl-5-[2-(methylsulfamoyl)propionyl]-4-(3-nitrophenyl)nicotinic acid 2-propoxyethyl ester, m.p. 120°-123° (yellow crystalline powder from ethanol, only one of the two possible racemates).

The 4-amino-N,1-dimethyl-2-oxo-4-pentenesulfonamide used as the starting material was prepared as follows:

A solution of 1.6 g of sodium hydroxide in 20 ml of water was added dropwise at 5°-12° with vigorous stirring to a solution of 3.5 g of 2,3-dimethyl-1,2-thiazin-5(6H)-one 1,1-dioxide, 6.8 g of tetrabutylammonium hydrogen sulfate and 1.9 ml (0.03 mol) of methyl iodide in 40 ml of methylene chloride. The mixture was thereafter stirred vigorously at room temperature for 15 minutes. The organic phase was separated, the aqueous phase was extracted twice with 15 ml of methylene chloride and the combined organic phases were washed with a saturated aqueous solution of sodium chloride, dried over sodium sulfate and concentrated to dryness. The oily residue was chromatographed on 300 g of silica gel with chloroform/n-heptane/ethanol (10:10:1) as the elution agent. The uniform fractions were combined and evaporated. After triturating the residue with ether there were obtained 1.8 g of 2,3,6-trimethyl-2H-1,2-thiazin-5(6H)-one 1,1-dioxide in the form of colorless crystals, m.p. 73°-75°.

A moderately rapid stream of dry ammonia was introduced at 20°-25° during 3 hours into a solution of 2.5 g of 2,3,6-trimethyl-2H-1,2-thiazin-5(6H)-one 1,1-dioxide in 25 ml of methanol and the mixture was thereupon left to stand overnight. The dark yellow solution obtained was concentrated to dryness under reduced pressure and the crystalline residue was recrystallized from ethanol. There were obtained 2.3 g of 4-amino-N,1-dimethyl-2-oxo-3-pentenesulfonamide in the form of colorless crystals, m.p. 140°-143°.

EXAMPLE 12

After boiling 2.8 g of 3-nitrobenzylideneacetoacetic acid isopropyl ester and 2.34 g of 4-amino-N-isopropyl-1-methyl-2-oxo-3-pentenesulfonamide in a mixture of 10 ml of isopropanol and 5 ml of dimethylformamide for 8 hours there were obtained 1.4 g of 1,4-dihydro-2,6-dimethyl-5-[2-(isopropylsulfamoyl)propionyl]-4-(3-nitrophenyl)nicotinic acid isopropyl ester, m.p. 155°–158° (yellow crystalline powder from ether, only one of the two possible racemates).

The 4-amino-N-isopropyl-1-methyl-2-oxo-3-pentenesulfonamide used as the starting material was prepared from 2-isopropyl-3-methyl-1,2-thiazin-5(6H)-one 1,1-dioxide as described in Example 11. There was firstly obtained 2-isopropyl-3,6-dimethyl-2H-1,2-thiazin-5(6H)-one 1,1-dioxide, m.p. 61°–65° (from ether), which was thereafter converted into 4-amino-N-isopropyl-1-methyl-2-oxo-3-pentenesulfonamide, m.p. 117°–120° (from ethanol).

EXAMPLE 13

After boiling 2.8 g of 3-nitrobenzylideneacetoacetic acid isopropyl ester and 2.34 g of N-isopropyl-4-methyl amino-2-oxo-3-pentanesulfonamide in a mixture of 25 ml of isopropanol and 12 ml of dimethylformamide for 16 hours there were obtained 1.2 g of 1,4-dihydro-5-[(isopropylsulfamoyl)acetyl]-1,2,6-trimethyl-4-(3-nitrophenyl)nicotinic acid isopropyl ester of melting point 67°–69° (yellow crystalline powder from ether). This product contained 0.5 mol of ether on the basis of the microanalysis and the NMR data.

The N-isopropyl-4-methylamino-2-oxo-3-pentenesulfonamide used as the starting material was prepared as follows:

A slow stream of dry methylamine was introduced at 20°–25° during 1 hour into a suspension of 4 g of 2-isopropyl-3-methyl-1,2-thiazin-5(6H)-one 1,1-dioxide in 40 ml of methanol, whereby a clear yellow solution resulted after about 30 minutes. Thereupon, the mixture was stirred further at room temperature for 5 hours, concentrated to dryness under reduced pressure and the crystalline residue was recrystallized from isopropyl. There were obtained 3.8 g of N-isopropyl-4-methylamino-2-oxo-3-pentenesulfonamide in the form of colorless crystals, m.p. 83°–85°.

EXAMPLE 14

A solution of 3.4 g of (±)-3-nitrobenzylideneacetoacetic acid 1-phenylethyl ester in a mixture of 10 ml of isopropanol and 5 ml of dimethylformamide was treated under argon with 2.20 g of 4-amino-N-isopropyl-2-oxo-3-pentenesulfonamide and the mixture was thereupon heated to reflux for 8 hours. After concentration under reduced pressure the oily residue was chromatographed on 300 g of silica gel with methylene chloride/ethyl acetate (4:1) as the elution agent. The homogeneous fractions yielded an oil (3.1 g) which consisted of a mixture of the two possible racemates of 1,4-dihydro-5-[(isopropylsulphamoyl)acetyl]-2,6-dimethyl-4-(3-nitrophenyl)nicotinic acid 1-phenylethyl ester on the basis of the NMR data.

For the separation of the two racemates, the oily product (3.1 g) was taken up in 100 ml of ether and the solution obtained was left to stand at room temperature overnight. The crystallized-out product was filtered off, washed with a small amount of ether and recrystallized from isopropanol, whereby there was obtained 0.70 g of the one pure racemate (racemate A) in the form of yellow crystals, m.p. 164°–166°. The ethereal mother liquor was concentrated to about 70 ml, left to stand overnight at room temperature and a small amount of the racemate mixture (about 0.2 g) was filtered off. The filtrate obtained was now concentrated to about 50 ml and again left to stand at room temperature overnight. The new precipitate yielded, after recrystallization from isopropanol, 0.50 g of the other pure racemate (racemate B) in the form of yellow crystals, m.p. 155°–157°.

EXAMPLE 15

A solution of 3.75 g of (±)-3-nitrobenzylideneacetoacetic acid 1-p-chlorophenylethyl ester and 2.20 g of 4-amino-N-isopropyl-2-oxo-3-pentenesulfonamide in a mixture of 10 ml of isopropanol and 5 ml of dimethylformamide was heated to reflux for 8 hours and thereafter concentrated to dryness under reduced pressure. The residual oil was chromatographed on 500 g of silica gel with methylene chloride/ethyl acetate (4:1) as the elution agent, whereby the two racemates of 1,4-dihydro-5-[(isopropylsulfamoyl)acetyl]-2,6-dimethyl-4-(3-nitrophenyl)nicotinic acid 1-p-chlorophenylethyl ester which were formed were separated. The homogenous fractions eluted firstly gave, after evaporation, trituration of the residue with ether and recrystallization from ethanol, 0.70 g of the one pure racemate in the form of yellow crystals, m.p. 155°–158°. The homogenous fractions which were eluted afterwards yielded, after the same treatment, 0.85 g of the second pure racemate in the form of yellow crystals, m.p. 148°–151°.

EXAMPLE 16

A solution of 6.8 g of (S)-3-nitrobenzylideneacetoacetic acid 1-phenylethyl ester in a mixture of 20 ml of isopropanol and 10 ml of dimethylformamide was treated under argon with 4.40 g of 4-amino-N-isopropyl-2-oxo-3-pentenesulfonamide and the mixture was thereupon heated to reflux for 8 hours. After concentration under reduced pressure the oily residue was chromatographed on 800 g of silica gel with methylene chloride/ethyl acetate (4:1) as the elution agent, whereby the two expected epimers were eluted as a mixture. The homogeneous fractions yielded an oil which was taken up in 300 ml of ether and left to stand at room temperature overnight. The crystallized-out product was filtered off, washed with a small amount of ether and recrystallized from ethanol. There were obtained 2.3 g of (R)-1,4-dihydro-5-[(isopropylsulfamoyl)acetyl]-2,6-dimethyl-4-(3-nitrophenyl)nicotinic acid (S)-1-phenylethyl ester in the form of yellow crystals, m.p. 151°–153°, specific rotation: $[\alpha]_{546}^{20} = +518°$ (c=1.0% w/v, ethanol). On the basis of the NMR spectrum this was the (+)-enantiomer of the racemate A described in Example 14.

The ethereal mother liquor obtained was concentrated to 200 ml and left to stand at room temperature for 2–3 days, whereby the second epimer formed crystallized slowly. After recrystallization from ethanol there were obtained 1.75 of (S)-1,4-dihydro-5-[(isopropylsulfamoyl)acetyl]-2,6-dimethyl-4-(3-nitrophenyl)nicotinic acid (S)-1-phenylethyl ester in the form of yellow crystals, m.p. 128°–131°, specific rotation: $[\alpha]_{546}^{20} = -163°$ (c=1.0% w/v, ethanol). On the basis of the NMR spectrum this was the (31)-enantiomer of the racemate B described in Example 14. The (S)-configuration given for the chiral centre in position 4 was determined by an X-ray structural analysis.

EXAMPLE 17

The following two epimers were obtained from (R)-3-nitrobenzylideneacetoacetic acid 1-phenylethyl ester and 4-amino-N-isopropyl-2-oxo-3-pentenesulfonamide in accordance with the procedure described in Example 16:

(S)-1,4-Dihydro-5-[(isopropylsulfamoyl)acetyl]-2,6-dimethyl-4-(3-nitrophenyl)nicotinic acid (R)-1-phenylethyl ester in the form of yellow crystals, m.p. 151°–153° (from ethanol), specific rotation: $[\alpha]_{546}^{20} = -512°$ (c=1.0% w/v, ethanol). On the basis of the NMR spectrum this was the (−)-enantiomer of the racemate A described in Example 14.

(R)-1,4-Dihydro-5-[(isopropylsulfamoyl)acetyl]-2,6-dimethyl-4-(3-nitrophenyl)nicotinic acid (R)-1-phenylethyl ester in the form of yellow crystals, m.p. 128°–131° (from ethanol), specific rotation: $[\alpha]_{546}^{20} = +165°$ (c=1.0% w/v, ethanol). On the basis of the NMR spectrum this was the (+)-enantiomer of the racemate B described in Example 14.

EXAMPLE 18

A solution of 2.35 g of 1,4-dihydro-5-[(isopropylsulfamoyl)acetyl]-2,6-dimethyl-4-(3-nitrophenyl)nicotinic acid ethyl ester in a mixture 25 ml of ethanol and 5 ml of dimethylformamide was treated portionwise at 15°–20° under argon with 0.20 g of sodium borohydride and the mixture was stirred at room temperature for a further 20 hours. Thereupon, the suspension obtained was adjusted cautiously to pH 4–5 with 1N hydrochloric acid and the ethanol was evaporated off under reduced pressure. The solution remaining was treated with approximately double the volume of ice and extracted with methylene chloride. The organic phase was washed with water, dried over sodium sulfate and concentrated to dryness. The residual oil was chromatographed on 600 g of silica gel with methylene chloride/ethyl acetate (4:1) as the elution agent. The uniform fractions were combined and evaporated. After triturating the residue with ether there were obtained 1.9 of 1,4-dihydro-5-[(E)-2-(isopropylsulfamoyl)vinyl]-2,6-dimethyl-4-(3-nitrobenzyl)nicotinic acid ethyl ester in the form of yellow crystals, m.p. 191°–193°. Recrystallization from ethanol did not increase the melting point.

EXAMPLE 19

Analogously to Example 18, 1.86 g of 5-[(ethylsulfamoyl)acetyl]-1,4-dihydro-2,6-dimethyl-4-(3-nitrophenyl)nicotinic acid isopropyl ester were treated with 0.16 g of sodium borohydride in a mixture of 20 ml of isopropanol and 4 ml of dimethylformamide. After chromatography with methylene chloride/ethyl acetate (4:1) as the elution agent there were obtained 1.5 g of 5-[(E)-2-(ethylsulfamoyl)vinyl]-1,4-dihydro-2,6-dimethyl-4-(3-nitrophenyl)nicotinic acid isopropyl ester in the form of yellow crystals, m.p. 187°–189°. Recrystallization from methylene chloride/ether did not increase the melting point.

EXAMPLE 20

Analogously to Example 18, a solution of 1.56 g of 1,4-dihydro-5-[(isopropylsulfamoyl)acetyl]-2,6-dimethyl-4-(3-nitrophenyl)nicotinic acid 2,2,2-trifluoroethyl ester in 15 ml of isopropanol was treated with 0.12 g (3 mmol) of sodium borohydride. After chromatography with methylene chloride/ethyl acetate (4:1) as the elution agent there were obtained 1.25 g of 1,4-dihydro-5-[(E)-2-(isopropylsulfamoyl)vinyl]-2,6-dimethyl-4-(3-nitrophenyl)nicotinic acid 2,2,2-trifluoroethyl ester in the form of yellow crystals, m.p. 180°–182°. Recrystallization from isopropanol did not increase the melting point.

EXAMPLE 21

Analogously to Example 18, 1.02 g of 4-(2-chloro-5-nitrophenyl)-1,4-dihydro-5-[(isopropylsulfamoyl)acetyl]-2,6-dimethylnicotinic acid isopropyl ester were treated with 0.08 g of sodium borohydride in a mixture of 10 ml of isopropanol and 2 ml of 1,2-dimethoxyethane. After chromatography with methylene chloride/ethyl acetate (4:1) as the elution agent there was obtained 0.70 g of 4-(2-chloro-5-nitrophenyl)-1,4-dihydro-5-[(E)-2-(isopropylsulfamoyl)vinyl]-2,6-dimethylnicotinic acid isopropyl ester in the form of yellow crystals, m.p. 199°–201°.

EXAMPLE 22

Analogously to Example 18, 1.05 g of 1,4-dihydro-5-[(isopropylsulfamoyl)acetyl]-2,6-dimethyl-4-(3-nitrophenyl)nicotinic acid 2-propoxyethyl ester were treated with 0.08 g of sodium borohydride in a mixture of 10 ml of ethanol and 2 ml of dimethylformamide. After chromatography with methylene chloride/ethyl acetate (4:1) as the elution agent there was obtained 0.90 g of 1,4-dihydro-5-[(E)-2-(isopropylsulfamoyl)vinyl]-2,6-dimethyl-4-(3-nitrophenyl)nicotinic acid 2-propoxyethyl ester in the form of yellow crystals, m.p. 152°–154°.

EXAMPLE 23

Analogously to Example 18, 1.03 g of 5-[(benzylmethylsulfamoyl)acetyl]-1,4-dihydro-2,6-dimethyl-4-(3-nitrophenyl)nicotinic acid methyl ester were treated with 0.08 g of sodium borohydride in a mixture of 10 ml of isopropanol and 4 ml of dimethylformamide. After chromatography with methylene chloride/ethyl acetate (4:1) as the elution agent there was obtained 0.64 g of 5-[(E)-2-(benzyl-methylsulfamoyl)vinyl]-1,4-dihydro-2,6-dimethyl-4-(3-nitrophenyl)nicotinic acid methyl ester in the form of yellow crystals, m.p. 208°–210°.

EXAMPLE 24

Analogously to Example 18, 1.08 g of (S)-1,4-dihydro-5-[(isopropylsulfamoyl)acetyl]-2,6-dimethyl-4-(3-nitrophenyl)nicotinic acid (R)-1-phenylethyl ester were treated with 0.08 g of sodium borohydride in a mixture of 10 ml of isopropanol and 2 ml of dimethylformamide. The product was chromatographed with methylene chloride/ethyl acetate (4:1) as the elution agent and then recrystallized from ethanol. There was obtained 0.82 g of (S)-1,4-dihydro-5-[(E)-2-(isopropylsulfamoyl)vinyl]-2,6-dimethyl-4-(3-nitrophenyl)nicotinic acid (R)-1-phenylethyl ester in the form of yellow crystals, m.p. 198°–201°, specific rotation: $[\alpha]_{546}^{20} = -290°$ (c=1.0% w/v, chloroform).

EXAMPLE 25

A solution of 4.12 g of N-ethyl-4-amino-2-oxo-3-pentenesulfonamide, 2.81 g of 2-chlorobenzaldehyde and 3.76 g of 4-acetoxyacetoacetic acid ethyl ester in a mixture of 20 ml of ethanol and 10 ml of dimethylformamide was heated to reflux under argon for 15 hours. The solution was then concentrated to dryness under reduced pressure and the residual oil was chromatographed on 360 g of silica gel with methylene chloride/ethyl acetate (4:1) as the elution agent. The homogeneous fractions were combined and evaporated. The residual oil crystallized upon trituration with ether. There were obtained 4.0 g of 2-acetoxymethyl-5-[(ethylsulfamoyl)acetyl]-4-(2-chlorophenyl)-1,4-dihydro-6-methylnicotinic acid ethyl aster in the form of yellow crystals, m.p. 106°–108°. Recrystallization from ethanol yielded a product of melting point 109°–110°.

EXAMPLE 26

A solution of 3.0 g of 1,4-dihydro-5-[(isopropylsulfamoyl)acetyl]-2,6-dimethyl-4-(3-nitrophenyl)-nicotinic acid 2-chloroethyl ester in 18 ml of dimethylformamide were treated under argon with 0.75 g of dry sodium acetate and the mixture was thereupon heated to reflux for 1 hour. The mixture was then concentrated to dryness under reduced pressure and the residue was partitioned between water and methylene chloride. The organic phase was washed with a saturated aqueous solution of sodium chloride, dried over sodium sulfate and evaporated to dryness. The residual oil was chromatographed on 300 g of silica gel with methylene chloride/ethyl acetate (4:1) as the elution agent. The uniform fractions were combined and evaporated. After triturating the residue with ether there were obtained 1.85 g of 1,4-dihydro-5-[(isopropylsulfamoyl)acetyl]-2,6-dimethyl-4-(3-nitrophenyl)nicotinic acid 2-acetoxyethyl ester in the form of pale yellow crystals, m.p. 133°–136°. Recrystallization from isopropanol yielded a product of melting point 134°–137°.

EXAMPLE 27

A suspension of 2.09 g of 1,4-dihydro-5-[(isopropylsulfamoyl)acetyl]-2,6-dimethyl-4-(3-nitrophenyl)nicotinic acid 2-acetoxyethyl ester in 20 ml of ethanol was treated dropwise at room temperature with a solution of 0.36 g of sodium hydroxide in 24 ml of ethanol. The dark orange solution obtained was subsequently stirred at room temperature for 1 hour. The ethanol was thereupon evaporated off at 25°–30° under reduced pressure and the residue was dissolved in 20 ml of water. The mixture was acidified cautiously with 2N hydrochloric acid, extracted several times with a mixture of methylene chloride/ethyl acetate (9:1) and the extract was dried over sodium sulfate. After evaporation of the solvent the solid residue was recrystallized from ethanol. There were obtained 1.55 g of 1,4-dihydro-5-[(isopropylsulfamoyl)acetyl]-2,6-dimethyl-4-(3-nitrophenyl)nicotinic acid 2-hydroxyethyl ester in the form of pale yellow crystals, m.p. 185°–188°.

EXAMPLE 28

The following compounds were made in an analogous manner to that described in Example 4:
1,4-Dihydro-5-[(isopropylsulfamoyl)acetyl]-2,6-dimethyl-4-(3-nitrophenyl)nicotinic acid cyclopentyl ester, m.p. 112°–115°, from 3-nitrobenzylideneacetoacetic acid cyclopentyl ester and 4-amino-N-isopropyl-2-oxo-3-pentenesulfonamide;
1,4-dihydro-5-[(isopropylsulfamoyl)acetyl]-2,6-dimethyl-4-(3-nitrophenyl)nicotinic acid cyclopropylmethyl ester, m.p. 152°–154°, from 3-nitrobenzylideneacetoacetic acid cyclopropylmethyl ester and 4-amino-N-isopropyl-2-oxo-3-pentenesulfonamide and
1,4-dihydro-5-[(isopropylsulfamoyl)acetyl]-2,6-dimethyl-4-(3-nitrophenyl)nicotinic acid 2-methylthioethyl ester, m.p. 121°–124°, from 3-nitrobenzylideneacetoacetic acid 2-methylthioethyl ester and 4-amino-N-isopropyl-2-oxo-3-pentenesulfonamide.

EXAMPLE A

Manufacture of tablets of the following composition:

| I. 1,4-Dihydro-5-[(isopropylsulfamoyl)-acetyl]-2,6-dimethyl-4-(3-nitrophenyl)-nicotinic acid 2-propoxyethyl ester micronized | 20.0 mg |
|---|---|
| Lactose powder | 40.0 mg |
| Maize starch white | 24.9 mg |
| II. Dioctyl sodium sulfosuccinate | 0.1 mg |
| Maize starch white | 5.0 mg |
| Water | q.s. |
| III. Maize starch white | 6.0 mg |
| IV. Talc | 3.0 mg |
| Magnesium stearate | 1.0 mg |
| | 100.0 mg |

The substances of phase I are sieved and mixed. This mixture is moistened with the maize starch paste II and kneaded. The moist mass is granulated, dried and converted into a suitable particle size. Phase III is admixed. This mixture is mixed with phase IV for a short time.

The ready-to-press mixture is pressed to tablets of 100 mg with a break-bar.

EXAMPLE B

Manufacture of tablets of the following composition:

| I. 4-(2-Chloro-5-nitrophenyl)-1,4-dihydro-5-[isopropylsulfamoyl)acetyl]-2,6-dimethylnicotinic acid isopropyl ester | 200.0 mg |
|---|---|
| Lactose Powder | 42.9 mg |
| Maize starch white | 50.0 mg |
| II. Dioctyl sodium sulfosuccinate | 0.1 mg |
| Maize starch white | 20.0 mg |
| Water | q.s. |
| III. Maize starch white | 30.0 mg |
| IV. Talc | 3.5 mg |
| Magnesium stearate | 3.5 mg |
| | 350.0 mg |

The substances of phase I are sieved and mixed. This mixture is moistened with the maize starch paste II and kneaded. The moist mass is granulated, dried and converted into a suitable particle size. Phase III is admixed. This mixture is mixed with phase IV for a short time.

The ready-to-press mass is pressed to tablets of 350 mg with a break-bar.

EXAMPLE C

Manufacture of capsules of the following composition:

| I. 1,4-Dihydro-5-[(isopropylsulfamoyl)acetyl]-2,6-dimethyl-4-(3-nitrophenyl)-nicotinic acid 2-propoxyethyl ester micronized | 20.0 mg |
|---|---|
| Lactose powder | 48.0 mg |
| II. Maize starch | 5.0 mg |
| Water | q.s. |
| III. Lactose crystals | 50.0 mg |
| Maize starch | 15.0 mg |
| IV. Talc | 10.0 mg |
| Magnesium stearate | 2.0 mg |
| | 150.0 mg |

The substances of phase I are sieved and mixed. This mixture is moistened with the maize starch paste II and kneaded. The moist mass is granulated, dried and converted into a suitable particle size. Phase III is admixed. This mixture is mixed with phase IV for a short time.

The capsule mixture is filled into size 2 capsules each containing 150 mg.

EXAMPLE D

An aqueous drop suspension of the following composition is manufactured:

|  | 5 mg of a compound of formula I per 1 ml |
|---|---|
| 1,4-Dihydro-5-[isopropylsulfamoyl)-acetyl]-2,6-dimethyl-4-(3-nitrophenyl)-nicotinic acid 2-propoxyethyl ester | 0.05 g |
| Sodium benzoate | 0.035 g |
| Saccharin sodium | 0.015 g |
| Acrylic acid polymerizate | 0.1–1.0 g |
| Saccharose | 3.5 g |
| Citric acid | 0.025 g |
| Polyoxyethylene stearate | 0.002–0.01 g |
| Sodium hydroxide | q.s. |
| Flavor | q.s. |
| Food coloring | q.s. |
| Water deionized ad | 10.0 ml |

EXAMPLE E

When the procedures described in Examples A–D are followed, tablets, capsules and injection preparations can be manufactured from the following, likewise preferred compounds:

1,4-Dihydro-5-[(isopropylsulfamoyl)acetyl]-2,6-dimethyl-4-(3-nitrophenyl)nicotinic acid isopropyl ester, 4-(2,5-dichlorophenyl)-1,4-dihydro-5-[(isopropylsulfamoyl)acetyl]-2,6-dimethylnicotinic acid isopropyl ester and (S)-1,4-dihydro-5-[(isopropylsulfamoyl)acetyl]-2,6-dimethyl-4-(3-nitrophenyl)nicotinic acid (S)-1-phenylethyl ester.

We claim:

1. A compound of the formula

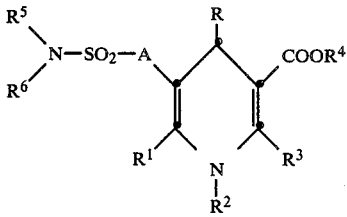

wherein A is —CH($R^7$)—CO— or

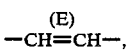

R is a mono- or bicyclic aromatic hydrocarbon residue with up to 10 carbon atoms in the aromatic ring structure which is optionally mono-, di- or tri-substituted by phenyl, $C_1$–$C_6$-alkyl, $C_3$–$C_6$-alkenyl, $C_3$–$C_6$-alkynyl, $C_1$–$C_6$-alkoxy, halogen, trifluoromethyl, trifluoromethoxy, difluoromethoxy, trifluoromethylthio, difluoromethylthio, nitro, cyano, azido, $C_1$–$C_6$-alkoxycarbonyl, aminocarbonyl, aminosulfonyl, $C_1$–$C_6$-alkylthio, $C_1$–$C_6$-alkylsulfonyl, or $C_1$–$C_6$-alkanoyl or which is optionally disubstituted by $C_3$–$C_5$-alkylene or dioxy-$C_1$–$C_2$-alkylene, $R^1$ is hydrogen or methyl, $R^2$ is hydrogen or $C_1$–$C_4$-alkyl, $R^3$ is $C_1$–$C_4$-alkyl or $C_1$–$C_4$-alkanoyloxymethyl, $R^4$ is $C_1$–$C_6$-alkyl, $C_3$–$C_6$-alkenyl, $C_3$–$C_6$-alkynyl, $C_3$–$C_6$-cycloalkyl, $C_3$–$C_6$-cycloalkyl-$C_1$–$C_6$-alkyl, cyano-$C_2$–$C_6$-alkyl, halo-$C_2$–$C_6$-alkyl, hydroxy-$C_2$–$C_6$-alkyl, $\omega,\omega,\omega$-trifluoro-$C_1$–$C_6$-alkyl, $C_1$–$C_6$-alkoxy-$C_1$–$C_6$-alkyl-, $C_1$—$C_6$-alkoxy-, $C_1$–$C_6$-alkoxy-$C_1$–$C_6$-alkyl, $C_1$–$C_4$-alkanoyloxy-$C_1$–$C_6$-alkyl, $C_3$–$C_6$-alkenyloxy-$C_1$–$C_6$-alkyl, $C_1$–$C_6$-alkylthio-$C_1$–$C_6$-alkyl, benzyloxy-$C_1$–$C_6$-alkyl, or is phenyl-$C_1$–$C_6$-alkyl optionally substituted by halogen, cyano, di-$C_1$–$C_6$-alkylamino, $C_1$–$C_6$-alkoxy, $C_1$–$C_6$-alkyl, trifluoromethyl or nitro, $R^5$ is $C_1$–$C_6$-alkyl or $C_3$–$C_6$-cycloalkyl, $R^6$ is hydrogen, $C_1$–$C_6$-alkyl, $C_3$–$C_6$-alkenyl, $C_3$–$C_6$-alkynyl, $C_3$–$C_6$-cycloalkyl, $C_3$–$C_6$-cycloalkyl-, $C_1$–$C_6$-alkyl or phenyl-$C_1$–$C_6$-alkyl optionally substituted by $C_1$–$C_6$-alkyl, $C_1$–$C_6$-alkoxy or halogen and $R^7$ is hydrogen, $C_1$–$C_6$-alkyl or phenyl-$C_1$–$C_6$-alkyl optionally substituted by $C_1$–$C_6$-alkyl, $C_1$–$C_6$-alkoxy, or halogen or $R^6$ and $R^7$ together with a —$(CH_2)_n$— group in which n is the number 2 or 3, in the form of isomers, isomer mixtures, racemates and optical antipodes.

2. A compound in accordance with claim 1, wherein $R^4$ is $C_1$–$C_6$-alkyl, cyano-$C_6$–$C_6$-alkyl, halo-$C_2$–$C_6$-alkyl, hydroxy-$C_2$–$C_6$-alkyl, $\omega,\omega,\omega$-trifluoro-$C_1$–$C_6$-alkyl, $C_1$–$C_6$-alkoxy-$C_1$–$C_6$-alkyl, $C_1$–$C_4$-alkanoyloxy-$C_1$–$C_6$-alkyl, benzyloxy-$C_1$–$C_6$-alkyl or phenyl-$C_1$–$C_6$-alkyl optionally substituted by halogen, $R^5$ is $C_1$–$C_6$-alkyl, $R^6$ is hydrogen, $C_1$–$C_6$-alkyl, $C_3$–$C_6$-alkenyl or phenyl-$C_1$–$C_6$-alkyl, $R^7$ is hydrogen or $C_1$–$C_6$-alkyl or $R^6$ and $R^7$ together are a —$(CH_2)_n$— group wherein n is the number 2 or 3 and R is naphthyl, phenyl optionally monosubstituted by $C_1$–$C_6$-alkyl, halogen, trifluoromethyl or nitro or optionally disubstituted by halogen or halogen and nitro.

3. A compound in accord in accordance with claim 2, wherein A is the group —CH($R^7$)—CO—.

4. A compound in accordance claim 3, wherein R is 3-nitrophenyl, 2-chloro-5-nitrophenyl or 2,5-dichlorophenyl, $R^1$ is methyl, $R^2$ is hydrogen and $R^3$ is $C_1$–$C_4$-alkyl.

5. A compound in accordance with claim 4, wherein $R^4$ is selected from the group consisting of isopropyl, 2,2,2-trifluoroethyl, 2-propoxyethyl or 1-phenylethyl, $R^5$ is $C_1$–$C_6$-alkyl preferably methyl, ethyl or isopropyl, and $R^6$ and $R^7$ each is hydrogen.

6. A compound in accordance with claim 5, wherein A is the group —CH($R^7$)—CO—, R is 3-nitrophenyl, 2-chloro-5-nitrophenyl or 2,5-dichlorophenyl, $R^1$ and $R^3$ each is methyl, $R^2$, $R^6$ and $R^7$ each is hydrogen, $R^4$ is isopropyl, 2,2,2-trifluoroethyl, 2-propoxyethyl or 1-phenylethyl and $R^5$ is methyl, ethyl or isopropyl.

7. A compound in accordance with claim 6, 5-[(Ethylsulfamoyl)acetyl]-1,4-dihydro-2,6-dimethyl-4-(3-nitrophenyl)nicotinic acid isopropyl ester.

8. A compound in accordance with claim 6, 1,4-Dihydro-2,6-dimethyl-5-[(methylsulfamoyl)-acetyl]-4-(3-nitrophenyl)nicotinic acid isopropyl ester.

9. A compound in accordance with claim 6, 1,4-Dihydro-2,6-dimethyl-5-[(methylsulfamoyl)-acetyl]-4-(3-nitrophenyl)nicotinic acid 2,2,2-trifluoroethyl ester.

10. A compound in accordance with claim 6, 4-(2-Chloro-5-nitrophenyl)-1,4-dihydro-5-[(isopropylsulfamoyl)acetyl]-2,6-dimethylnicotinic acid isopropyl ester.

11. A compound in accordance with claim 6, 4-(2,5-Dichlorophenyl)-1,4-dihydro-5-[(isopropylsulfamoyl)acetyl]-2,6-dimethylnicotinic acid isopropyl ester.

12. A compound in accordance with claim 6 1,4-Dihydro-5-[(isopropylsulfamoyl)acetyl]-2,6-dimethyl-4-(3-nitrophenyl)nicotinic acid 2-propoxyethyl ester.

13. A compound in accordance with claim 6, (S)-1,4-Dihydro-5-[(isopropylsulfamoyl)acetyl]-2,6-dimethyl-4-(3-nitrophenyl)nicotinic acid (S)-1-phenylethyl ester.

14. A compound in accordance with claim 2, 1,4-dihydro-5-[(E)-2-(isopropyl-sulfamoyl)vinyl]-2,6-dimethyl-4-(3-nitrophenyl)-nicotinic acid ethyl ester.

15. A compound in accordance with claim 2, 5-[(E)-2-(ethylsulfamoyl)vinyl]-1,4-dihydro-2,6-dimethyl-4-(3-nitrophenyl)nicotinic acid isopropyl ester.

16. A compound in accordance with claim 2, 1,4-dihydro-5-[(E)-2-(isopropylsulfamoyl)vinyl]-2,6-dimethyl-4-(3-nitrophenyl)nicotinic acid 2,2,2-trifluoroethyl ester.

17. A compound of the formula

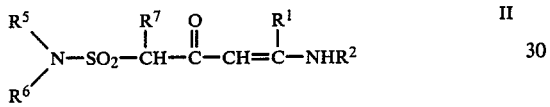

wherein $R^1$ is hydrogen or methyl, $R^2$ is hydrogen or $C_1$–$C_4$-alkyl, $R^5$ is $C_1$–$C_6$-alkyl or $C_3$–$C_6$-cycloalkyl, $R^6$ is hydrogen, $C_1$–$C_6$-alkyl, $C_3$–$C_6$-alkenyl, $C_3$–$C_6$-alkynyl, $C_3$–$C_6$-cycloalkyl, $C_3$–$C_6$-cycloalkyl-$C_1$–$C_6$-alkyl or phenyl-$C_1$–$C_6$-alkyl optionally substituted by $C_1$–$C_6$-alkyl, $C_1$–$C_6$-alkoxy or halogen and $R^7$ is hydrogen, $C_1$–$C_6$-alkyl or phenyl-$C_1$–$C_6$-alkyl optionally substituted by $C_1$–$C_6$-alkyl, $C_1$–$C_6$-alkoxy or halogen or $R^6$ and $R^7$ together are a —$(CH_2)_n$— group wherein n is the number 2 or 3.

18. A compound in accordance with claim 17, wherein $R^6$ is hydrogen.

19. A compound in accordance with claim 17, wherein $R^6$ is $C_1$–$C_6$-alkyl, $C_3$–$C_6$-alkenyl, $C_3$–$C_6$-alkynyl, $C_3$–$C_6$-cycloalkyl, $C_3$–$C_6$-cycloalkyl-, $C_1$–$C_6$-alkyl or phenyl-$C_1$–$C_6$-alkyl optionally substituted by $C_1$–$C_6$ alkyl, $C_1$–$C_6$-alkoxy or halogen.

20. A compound in accordance with claim 18, 4-amino-N-isopropyl-2-oxo-3-pentenesulfonamide.

21. A compound in accordance with claim 19, 4-amino-N,N-dimethyl-2-oxo-3-pentenesulfonamide.

22. The compound 1,4-dihydro-5-[(isopropylsulfamoyl)acetyl]-2,6-dimethyl-4-(3-pyridyl)nicotinic acid isopropyl ester.

23. A pharmaceutical composition for controlling or preventing angina pectoris, ischemia, high blood pressure or migraine comprising an amount, effective for the control or prevention of angina pectoris, ischemia, high blood pressure or migraine, of a compound of the formula

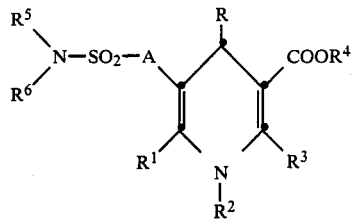

wherein A is —$CH(R^7)$—CO— or

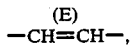

—CH=CH—,

R is a mono- or bicyclic aromatic hydrocarbon residue with up to 10 carbon atoms in the aromatic ring struture which is optionally mono-, di- or tri-substituted by phenyl, $C_1$–$C_6$-alkyl, $C_3$–$C_6$-alkenyl, $C_3$–$C_6$-alkynyl, $C_1$–$C_6$-alkoxy, halogen, trifluoromethyl, trifluoromethoxy, difluoromethoxy, trifluoromethylthio, difluoromethylthio, nitro, cyano, azido, $C_1$–$C_6$-alkoxycarbonyl, aminocarbonyl, aminosulfonyl, $C_1$–$C_6$-alkylthio, $C_1$–$C_6$-alkylsulfonyl, or $C_1$–$C_6$-alkanoyl or which is optionally disubstituted by $C_3$–$C_5$-alkylene or dioxy-$C_1$–$C_2$-alkylene, $R^1$ is hydrogen or methyl, $R^2$ is hydrogen or $C_1$–$C_4$-alkyl, $R^3$ is $C_1$–$C_4$-alkyl or $C_1$–$C_4$-alkanoyloxymethyl, $R^4$ is $C_1$–$C_6$-alkyl, $C_3$–$C_6$alkenyl, $C_3$–$C_6$-alkynyl, $C_3$–$C_6$-cycloalkyl, $C_3$–$C_6$-cycloalkyl-$C_1$–$C_6$-alkyl, cyano-$C_2$–$C_6$-alkyl, halo-$C_2$–$C_6$-alkyl, hydroxy-$C_2$–$C_6$-alkyl, $\omega,\omega,\omega$-trifluoro-$C_1$–$C_6$-alkyl, $C_1$–$C_6$-alkoxy-$C_1$–$C_6$alkyl-, $C_1$–$C_6$-alkoxy-$C_1$–$C_6$-alkoxy-$C_1$–$C_6$-alkyl, $C_1$–$C_4$-alkanoyloxy-$C_1$–$C_6$-alkyl, $C_3$–$C_6$-alkenyloxy-$C_1$–$C_6$-alkyl, $C_1$–$C_6$-alkylthio-$C_1$–$C_6$-alkyl, benzyloxy-$C_1$–$C_6$-alkyl, or is phenyl-$C_1$–$C_6$-alkyl optionally substituted by halogen, cyano, di-$C_1$–$C_6$-alkylamino, $C_1$–$C_6$-alkoxy, $C_1$–$C_6$-alkyl, trifluoromethyl or nitro, $R^5$ is $C_1$–$C_6$-alkyl or $C_3$–$C_6$-cycloalkyl, $R^6$ is hydrogen, $C_1$–$C_6$-alkyl, $C_3$–$C_6$-alkenyl, $C_3$–$C_6$-alkynyl, $C_3$–$C_6$-cylcoalkyl, $C_3$–$C_6$-cycloalkyl-$C_1$–$C_6$-alkyl or phenyl-$C_1$–$C_6$-alkyl optionally substituted by $C_1$–$C_6$-alkoxy or halogen and $R^7$ is hydrogen, $C_1$–$C_6$-alkyl or phenyl-$C_1$–$C_6$-alkyl optionally substituted by $C_1$–$C_6$-alkyl, $C_1$–$C_6$-alkoxy or halogen or $R^6$ and $R^7$ together are a —$(CH_2)_n$— group in which n is the number 2 or 3, in the form of an isomer, an isomer mixture, a racemate or an optical antipode and a pharmaceutically acceptable carrier material.

24. A composition in accordance with claim 23, wherein A is the group —$CH(R^7)CO$—.

25. A composition in accordance with claim 24 wherein A is the group —$CH(R^7)$—CO—, R is 3-nitrophenyl, 2-chloro-5-nitrophenyl or 2,5-dichlorophenyl, $R^1$ and $R^3$ each is methyl, $R^2$, $R^6$ and $R^7$ each is hydrogen, $R^4$ is isopropyl, 2,2,2-trifluoroethyl, 2-propoxyethyl or 1-phenylethyl and $R^5$ methyl, ethyl or isopropyl.

26. A composition in accordance with claim 25 wherein the compound of formula I is 1,4-dihydro-5-[(isopropylsulfamoyl)acetyl]-2,6-dimethyl-4-(3-nitrophenyl)nicotinic acid 2-propoxyethyl ester.

27. A method of controlling or preventing angina pectoris, ischemia, high blood pressure or migraine, which comprises administering to a warm-blooded animal in need thereof, an effective amount of a compound of the formula

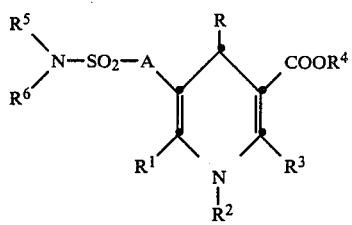

wherein A is —CH(R$^7$)—CO— or

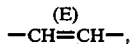

R is a mono- or bicyclic aromatic hydrocarbon residue with up to 10 carbon atoms in the aromatic ring structure which is optionally mono-, di- or tri-substituted by phenyl, $C_1$–$C_6$-alkyl, $C_3$–$C_6$-alkenyl, $C_3$–$C_6$-alkynyl, $C_1$–$C_6$-alkoxy, halogen, trifluoromethyl, trifluoromethoxy, difluoromethoxy, trifluoromethylthio, difluoromethylthio, nitro, cyano, azido, $C_1$–$C_6$-alkoxycarbonyl, aminocarbonyl, aminosulfonyl, $C_1$–$C_6$-alkylthio, $C_1$–$C_6$-alkylsulfonyl, or $C_1$–$C_6$-alkanoyl or which is optionally disubstituted by $C_3$–$C_5$-alkylene or dioxy-$C_1$–$C_2$-alkylene, $R^1$ is hydrogen or methyl, $R^2$ is hydrogen or $C_1$–$C_4$-alkyl, $R^3$ is $C_1$–$C_4$-alkyl or $C_1$–$C_4$-alkanoyloxymethyl, $R^4$ is $C_1$–$C_6$-alkyl, $C_3$–$C_6$-alkenyl, $C_3$–$C_6$-alkynyl, $C_3$–$C_6$-cycloalkyl, $C_3$–$C_6$-cycloalkyl-$C_1$–$C_6$alkyl, cyano-$C_2$–$C_6$-alkyl, halo-$C_2$–$C_6$-alkyl, hydroxy-$C_2$–$C_6$-alkyl, $\omega,\omega,\omega$-trifluoro-$C_1$–$C_6$-alkyl, $C_1$–$C_6$-alkoxy-$C_1$–$C_6$-alkyl-$C_1$–$C_6$-alkoxy-$C_1$–$C_6$-alkoxy-$C_1$–$C_6$-alkyl, $C_1$–$C_4$-alkanoyloxy-$C_1$–$C_6$-alkyl, $C_3$–$C_6$-alkenyloxy-$C_1$–$C_6$-alkyl, $C_1$–$C_6$alkylthio-$C_1$–$C_6$-alkyl, benzyloxy-$C_1$–$C_6$-alkyl, or is phenyl-$C_1$–$C_6$-alkyl optionally substituted by halogen, cyano, di-$C_1$–$C_6$-alkylamino, $C_1$–$C_6$-alkoxy, $C_1$–$C_6$-alkyl, trifluoromethyl or nitro, $R^5$ is $C_1$–$C_6$-alkyl or $C_3$–$C_6$-cycloalkyl, $R^6$ is hydrogen, $C_1$–$C_6$-alkyl, $C_3$–$C_6$-alkenyl, $C_3$–$C_6$-alkynyl, $C_3$–$C_6$-cylcoalkyl, $C_3$–$C_6$-cycloalkyl-$C_1$–$C_6$-alkyl or phenyl-$C_1$–$C_6$-alkyl optionally substituted by $C_1$–$C_6$-alkyl, $C_1$–$C_6$-alkoxy or halogen and $R^7$ is hydrogen, $C_1$–$C_6$-alkyl or phenyl-$C_1$–$C_6$-alkyl optionally substituted by $C_1$–$C_6$-alkyl, $C_1$–$C_6$-alkoxy or halogen or $R^6$ and $R^7$ together are a —$(CH_2)_n$— group in which n is the number 2 or 3, in the form of an isomer, isomer mixture, a racemate or an optical antipode.

28. A method in accordance with claim 27, wherein A is the group —CH(R$^7$)CO—.

29. A method in accordance with claim 28 wherein A is the group —CH(R$^7$)—CO—, R is 3-nitrophenyl, 2-chloro-5-nitrophenyl or 2,5-dichlorophenyl, $R^1$ and $R^3$ each is methyl, $R^2$, $R^6$ and $R^7$ each is hydrogen, $R^4$ is isopropyl, 2,2,2-trifluoroethyl, 2-propoxyethyl or 1-phenylethyl and $R^5$ methyl, ethyl or isopropyl.

30. A method in accordance with claim 29 wherein the compound of formula I is 1,4-dihydro-5-[isopropylsulfamoyl)acetyl]-2,6-dimethyl-4-(3-nitrophenyl)nicotinic acid 2-propoxyethyl ester.

* * * * *